US012575963B2

(12) United States Patent
Rhodes

(10) Patent No.: US 12,575,963 B2
(45) **Date of Patent: *Mar. 17, 2026**

(54) APPARATUS THAT ENABLES NON-PENETRATING SEX

(71) Applicant: Merlin's Sleeve LLC, San Diego, CA (US)

(72) Inventor: James Rhodes, La Jolla, CA (US)

(73) Assignee: Merlin's Sleeve LLC, San Diego, CA (US)

( * ) Notice: Subject to any disclaimer, the term of this patent is extended or adjusted under 35 U.S.C. 154(b) by 133 days.

This patent is subject to a terminal disclaimer.

(21) Appl. No.: 18/774,221

(22) Filed: Jul. 16, 2024

(65) Prior Publication Data

US 2024/0366420 A1 Nov. 7, 2024

Related U.S. Application Data

(63) Continuation of application No. 18/313,299, filed on May 5, 2023, now Pat. No. 12,036,145, which is a (Continued)

(51) Int. Cl.

*A61F 6/04* (2006.01)
*A41B 9/12* (2006.01)

(Continued)

(52) U.S. Cl.

CPC ................ *A61F 6/065* (2013.01); *A41B 9/12* (2013.01); *A61H 19/30* (2013.01); *A61F 6/04* (2013.01);

(Continued)

(58) Field of Classification Search

CPC .... A61F 6/065; A61F 6/06; A61F 6/04; A61F 2006/041; A41B 9/026; A41B 9/005;

(Continued)

(56) References Cited

U.S. PATENT DOCUMENTS 4,820,291 A * 4/1989 Terauchi ................ A61F 5/451
4/144.3
4,966,165 A * 10/1990 Anderson .............. A61F 6/065
128/830

(Continued)

*Primary Examiner* — Camtu T Nguyen
(74) *Attorney, Agent, or Firm* — ARC IP Law, PC; Joseph J. Mayo

(57) ABSTRACT

Apparatus that enables non-penetrating sex between two users. Embodiments may be integrated into or attached to clothing worn by the first user. A tubular element (including, but not limited to, a male or female condom) may be installed either permanently or detachably; attachments at both the open and closed ends of the tubular element ensure that it will not penetrate the first user. Users may therefore enjoy many of the benefits of sex, including intimacy and mutual stimulation, without the risks inherent in penetration. Attachment for the open end may use for example an element that attaches to a base ring or flange at the open end. Illustrative attachments for the closed end include a loop into which the closed end is cinched, a notch or hole into which a button in the closed end is inserted, and a mechanism into which the closed end is inserted, folded, and secured.

20 Claims, 28 Drawing Sheets

Related U.S. Application Data continuation of application No. 17/515,671, filed on Nov. 1, 2021, now Pat. No. 11,642,239, which is a continuation of application No. 16/722,777, filed on Dec. 20, 2019, now Pat. No. 11,229,546, which is a continuation of application No. 16/040,284, filed on Jul. 19, 2018, now Pat. No. 10,512,563.

(60) Provisional application No. 62/534,509, filed on Jul. 19, 2017.

(51) Int. Cl.
*A61F 6/06* (2006.01)
*A61H 19/00* (2006.01)

(52) U.S. Cl.
CPC ... *A61F 2006/041* (2013.01); *A61F 2006/047* (2013.01)

(58) Field of Classification Search
CPC ........... A41B 9/004; A41B 9/023; A41B 9/04; A41B 9/02; A41B 9/12
See application file for complete search history.

(56) References Cited

U.S. PATENT DOCUMENTS 5,346,483 A * 9/1994 Thaxton, Sr. ........... A61F 5/453
600/580
2022/0071799 A1 * 3/2022 Moten ....................... A61F 6/04

* cited by examiner

APPARATUS THAT ENABLES NON-PENETRATING SEX

This application is a Continuation of U.S. Utility patent Ser. No. 18/313,299, filed 5 May 2023, issued as U.S. Pat. No. 12,036,145 on 16 Jul. 2024, which is a Continuation of U.S. Utility patent Ser. No. 17/515,671, filed 1 Nov. 2021, issued as U.S. Pat. No. 11,642,239 on 9 May 2023, which is a Continuation of U.S. Utility patent Ser. No. 16/722,777, filed 20 Dec. 2019, issued as U.S. Pat. No. 11,229,546 on 25 Jan. 2022, which is a Continuation of U.S. Utility patent Ser. No. 16/040,284, filed 19 Jul. 2018, issued as U.S. Pat. No. 10,512,563 on 24 Dec. 2019, which claims the benefit of U.S. Provisional Patent Application 62/534,509, filed 19 Jul. 2017, the specifications of which are hereby incorporated herein by reference.

BACKGROUND OF THE INVENTION

Field of the Invention

One or more embodiments of the invention are related the following fields of use: contraception, prophylaxis, and condoms; adult entertainment and novelty devices; undergarments; and garment fastenings.

Description of the Related Art

Know sex devices such as sheaths and condoms or garments that include tubular elements generally provide for a protective barrier that is used for penetrative sex. There are many situations where penetration raises the prospect for various types of hazards, including physical, biological, interpersonal, emotional, developmental, ethanol, religious, and legal hazards.

For example, there exists latex panties that include a tubular element that may be inserted into an orifice in a user that is wearing the panties. In this situation, the garment is acting as stationary condom with respect to the user wearing the panties, e.g., such as a female condom works. This type of garment does not attach to the closed end of the tubular element and thus enables penetrative sex. U.S. Pat. No. 5,687,741 for example in FIG. 3 shows the penetrative configuration.

U.S. Patent Application Publication 2017/0042726 discloses a device that utilizes tubular elements, such as “fluid-impenetrable receiver 104” that are always on the outside of a garment. For example, the closed end of the tubular element is always on the outside of garment 102 for example. This may prevent penetrative sex, but also requires a special tubular element, i.e., not a cheap and replaceable condom, and also is located on the outside of the garment. Based on the thickness of the garment, the location of the tubular element on the outside of the garment may not provide for heat from the wearer’s body and may not provide compressive benefits close to the wearer’s skin for example. U.S. Pat. No. 5,620,429 attaches the closed end of the tubular element to a pad and does not place the tubular element on an interior portion of a garment, here a pad, and hence does not minimize the distance between the users, does not enable heat to transfer between the users and diminishes the observed compressive force between the two users, e.g., if there was no pad. In addition, the tubular elements in these devices are not condoms and thus cannot be cheaply or quickly replaced after use.

For at least the limitations described above and to avoid the problems listed above, there is a need for an apparatus that enables non-penetrating sex.

BRIEF SUMMARY OF THE INVENTION

One or more embodiments described in the specification are related to an apparatus that enables non-penetrating sex.

Sexual activity is a fundamental to reproduction and life, an important component of interpersonal relationships, and a source of emotional and physical pleasure, satisfaction, and fulfillment. Despite its fundamental roles, benefits, and desirability, sexual activity raises the prospect for various types of hazards, including physical, biological, interpersonal, emotional, developmental, ethanol, religious, and legal hazards. The need to balance the risks and benefits of sexual activity has inspired a long history of innovation related to the expression of human sexuality. Innovations related to addressing this area of natural tension have focused on aspects ranging from health and safety to clothing and wearable technology to pleasure enhancement.

One or more embodiments of the current invention represent an advancement in these fields. They may provide new options for engaging in sexual activity and increasing the benefits of sexual activity with lower exposure to various inherent hazards.

One or more embodiments are directed to problems associated with birth control and managing various hazards of sex and intercourse, including but not limited to physical, biological, interpersonal, emotional, developmental, ethical, religious, and/or legal hazards. In particular, one or more embodiments enable users to experience many of the benefits of sex (including but not limited to closeness, intimacy, interpersonal connection, and physical pleasure) without engaging in penetration of the vagina, anus, mouth, or other body parts.

The ability to enjoy the benefits of sex without engaging in penetrating sexual activity may be desirable for a variety of reasons, depending on the situational context and particular circumstances of the parties involved. For example, the parties may want to avoid engaging in penetrating sexual activity because of a combination of their relationship status and ethical or religious beliefs. Alternatively, one or more of the parties may have a physical or medical condition that makes penetrating sexual activity undesirable. Alternatively, penetrating sexual activity may be beyond the scope of activities agreed by the parties or allowed by law, which may be particularly relevant in the context of adult entertainment, for example.

One or more embodiments provide a way to engage in non-penetrating sexual activity. One or more embodiments may comprise a device or combination of devices that may be worn by a first user, and that comprises a tubular, sheath-like, or sleeve-like element or device configured to enable the insertion of the penis of a second user. The device(s) may be, but need not necessarily be, configured such that the first user’s genitals may be externally stimulated by the insertion and movement of the second user’s penis into the tubular element.

In some embodiments, the stimulation of both users may be enhanced by configuring the tubular element to be positioned such that the length of the tubular element rests between the first user’s body and the balance of the device or a garment, for example, and by further configuring the tubular element to be constructed from a relatively thin material—e.g., similar in thickness to a conventional condom. Such configurations can be structured so that the balance of the device or the garment provide a compressive force against both the tubular element and the first user's body. This compression may benefit both users by enhancing the stimulation of their respective body parts and by enhancing the transmission of sensations between their body parts. The external compressive force on the tubular element—created by the balance of the device or garment and the first user's body—may also reduce the need for the tubular element to generate a compressive force of its own on the second user's member. The ability for such configurations to relax this requirement enables the tubular element to be constructed from a relatively thin material, similar to the thickness of a condom. The use of such a thin material both further enhances the transmission of sensations between the users and enables the device to have a physical profile and weight similar to ordinary clothing, providing a substantial improvement on prior technologies. Such benefits may be provided where the device has multiple layers of material, with layers away from the first user providing compressive force against the tubular element and the first user's body, and with layers between the tubular element and the first user's body acting like a liner that provides additional barriers between the user's body parts.

The device(s) may be further configured such that insertion of the penis and movement of the user's bodies mimic in many respects the body positions and movements associated with penetrating sexual activity. As a result, a first user may enjoy the various benefits of sexual activity, including in some cases external stimulation of their genitals by the insertion of a second user's penis into the tubular element, without any part of their body being penetrated by the second user's penis. Meanwhile, the second user may enjoy the various benefits of sexual activity, including physical stimulation of their penis similar to what may result from penetrating sexual activity, without inserting their penis into any part of the first user's body.

One or more embodiments may include one or more devices that may be worn by, connected to or at least partially controlled by a first user and that have at least one integrated tubular element into which a second user's penis may be inserted and that is at least partially controlled by the first user. Multiple types of elements and mechanisms can be implemented within the scope of the invention to enable the device(s) to be worn by, connected to, or otherwise at least partially controlled by a first user. For example, the device(s) or one or more elements of the device(s) may be constructed from materials that enable sanitary cleaning between uses and therefore constitute multi-use device(s). Alternatively, the device(s) may be constructed from disposable materials and constitute single use device(s). Separately, the device(s) may be configured to be independently wearable (e.g., configured to resemble underwear or another garment) or may rely on one or more connections or attachments to another garment or device that is worn by or controlled by a first user.

One or more embodiments may include one or more devices that may be worn by, connected to, or at least partially controlled by a first user that enables temporary attachment of a detachable device with a tubular element into which a second user's penis may be inserted and that is at least partially controlled by a first user. The detachable device with a tubular element may comprise a conventional device, including but not limited to a condom or a male masturbation aid, for example. In such cases, these embodiments may comprise any or all of: (i) the device(s) that may be worn by, connected to, or at least partially controlled by the first user and that enable temporary attachment of the device with a tubular element; (ii) the enabling mechanisms of these devices; and (iii) the system of devices resulting from the combination of the two or more devices.

Alternatively, in one or more embodiments the detachable device with a tubular element may also comprise a novel device with a tubular element and with elements specifically configured to enable temporary attachment to the device(s) that may be worn, connected to, or at least partially controlled by the first user. One or more embodiments may also include at least the novel tubular device with elements configured to enable its temporary attachment to one or more devices that may be worn by, connected to, or at least temporary controlled by a first user.

One or more embodiments may include any or all of (i) one or more mechanisms to attach to a first user to connect to the garments of a first user, or to otherwise enable at least partial control of position or movement by a first user or by another device and (ii) a tubular element, sleeve, or sheath that is open on at least one end and is configured to enable the insertion of a second user's penis without penetrating any body part of the first user. Some embodiments may be positioned and configured to enable the vagina, clitoris or other parts of the first user to be physically stimulated by the second user's penis penetration of the tubular element or by another element or mechanism. In one or more embodiments, the device may comprise any or all of a device, a system of devices, or novel components that may be used in combination with other devices.

One of more embodiments may comprise a novel tubular element similar in certain respects to conventional male or female type condoms and configured to enable releasable attachment or coupling of the open and closed ends to a device worn by a first user to enable non-penetrating sex; the tubular element comprising a functional length of eight (8) inches or more, similar to a conventional male condom; a material thickness and material strength similar to that of a conventional female condom; an open end with a relatively wide base ring of a rigidity and diameter similar to a conventional female condom, enabling simplified coupling of the open end to a device or garment through the use of an opening in a surface of the device or garment that is relatively narrow in at least one direction; the closed end of the tubular element being releasably coupled to the garment or device using one or more attachment mechanisms, including but not limited to one or more mechanisms utilizing a relatively small size insert element.

One or more embodiments may comprise a device that (i) has elements enabling it to be worn by a first user, connected to the garments of a first user, or otherwise enabling at least partial control of the device's position and/or movement by a first user and (ii) has a tubular, sheath-like, or sleeve-like element sized and/or otherwise configured to enable insertion of the penis of a second user without the second user's penis penetrating the vagina, anus, or other body parts of the first user.

One or more embodiments may comprise a device that enables a first user to be directly or indirectly connected to or to otherwise control the position and/or movement of a separate device that comprises a tubular, sheath-like, or sleeve-like element into which the penis of a second user may be inserted. Such separate devices with tubular elements may for example enable a first user to be connected to or to otherwise exert at least partial control include but are not limited to condoms and male masturbation aids. One or more embodiments may be or may include a device or garment that is directly worn by the first user. One or more embodiments may be or may include a device that may be temporarily connected to a garment that is worn by the first user. One or more embodiments may be or may include a device that is permanently installed in garments worn by a first user. In one or more embodiments, all or a portion of the embodiment may be controlled by the first user's hands or by a combination of the first user's hands and other body parts, garments, or devices.

One or more embodiments may comprise a device that may be worn by or attached to a first user that has a tubular, sheath-like, or sleeve-like element configured to enable a second user to have non-penetrating sexual activity with the first user and/or to simulate having sex with the first user. The device may enable such non-penetrating sexual activity without requiring the first user to directly touch the second user's penis or, in some embodiments and applications, the tubular element.

One or more embodiments may comprise a device having one or more elements enabling a first user to at least partially control the position and/or movement of a tubular, sheath-like, or sleeve-like element configured such that a second user's penis may be inserted into it without enabling the second user's penis to penetrate any part of the first user's body. In one or more embodiments the first user may therefore be a "controlling user" who may fully or partially control movement. In one or more embodiments this "controlling user" may also be a "receiving user" who may for example wear a device that is used in non-penetrating sex. In one or more embodiments this "controlling user" may not wear any device, but may fully or partially control movement of a device into which the second user's penis may be inserted.

One or more embodiments may include an apparatus that enables non-penetrating sex between a first user and a second user. The apparatus may have two elements that couple with a tubular element, where the first element has an opening that couples with the open end of the tubular element, and the second element couples with the closed end of the tubular element. The coupling at either end may be fixed or releasable. The second element may couple to an external portion of the first user's body, either directly or indirectly. The closed end of the tubular element may be located on an inner portion of a garment that is in contact with the first user. When coupled to the two elements, the open and closed ends of the tubular element may be immobilized relative to the first user when the second user moves a member in and out of the tubular element during non-penetrating sex. The apparatus may therefore ensure that the tubular element remains outside of all orifices of the first user, so that the sex is non-penetrating.

One or more embodiments may include a garment that is coupled directly or indirectly to the first user. The garment may have an interior surface facing the first user, and an exterior surface facing away from the first user. The exterior surface may have a hole, with the opening in the first element collocated with the hole at least on the exterior surface.

In one or more embodiments the tubular element may be or may include a condom, and the first and second elements may couple releasably with the condom. In one or more embodiments that couple with a condom, the closed end of the condom when coupled may be on the inside, within, or on the outside of a garment that is in contact with the first user. One or more embodiments that couple with a condom may immobilize the open and closed ends of the condom relative to the first user when the second user moves a member in and out of the condom during non-penetrating sex. The apparatus may therefore ensure that the condom remains outside of all orifices of the first user, so that the sex is non-penetrating.

One or more embodiments that couple with a condom may include a garment that is coupled directly or indirectly to the first user. The garment may have an interior surface facing the first user, and an exterior surface facing away from the first user. The exterior surface may have a hole, with the opening in the first element collocated with the hole at least on the exterior surface.

One or more embodiments may couple with a male condom, with a female condom, or with either. In one or more embodiments that couple with a male condom, the condom may be inside-out to expose inner lubrication, so that the second user can readily move in and out of the condom when it is attached at the open and closed ends.

In one or more embodiments the first element may include an annular ramp, for example around the opening. The ramp may for example improve comfort and fit. The ramp may for example be flexible and may for example contain an elastomeric material.

In one or more embodiments the first element may have a flange that couples with the open end of a condom. The flange may be a segmented flange.

In one or more embodiments the first element may have a flange and a ring. The ring and flange may couple to the open end of the condom, for example via elastic force on the condom when it is placed between the ring and the flange.

In one or more embodiments the first element may have an opening that is smaller than the open end of the condom.

In one or more embodiments the first element may have hooks. The hooks may for example secure the base ring of a condom that is stretched around the hooks.

In one or more embodiments the condom may be coupled to the second element at the closed end by placing a small object inside the condom, and securing this item at the closed end with a coupling mechanism. The coupling mechanism may be for example a notch that is smaller than the small object, or a button hole through which the small object fits.

In one or more embodiments the condom may be coupled to the second element at the closed end using a loop, with the closed end secured by cinching the condom with the loop.

In one or more embodiments the condom may be coupled to the second element at the closed end with a roller.

In one or more embodiments the coupling element of the second element may have a surface that folds in two dimensions, a loop across one side of the surface, and an attachment mechanism to secure a left portion of the surface to a right portion of the surface.

In one or more embodiments the condom may have a line (such as a string for example) that extends from the closed end. The second element may couple to the closed end by attaching to the line.

In one or more embodiments the first element may couple to a waistband using connection elements that extend from the first element to the waistband. The second element may couple to the waistband on or near either the front portion or rear portion of the waistband.

In one or more embodiments the first element may couple to a garment in a front and rear portion of the first user, with material that may extend from the first element to at least one leg of the first user. The second element may couple to the first user at a location distal to the first element.

In one or more embodiments the first element may be located on an outer portion of a garment, and the second element may be located on an inner portion of the garment.

In one or more embodiments the first element may have a ring with a groove, where the ring surrounds the opening. The condom may be coupled by placing the condom's base ring into the groove.

In one or more embodiments the first element may have a ring with multiple beads connected by elastic. The ring may expand to fit different sizes of condoms or members of the second user.

In one or more embodiments the condom may have one or both of a base ring and a flange at the open end of the condom. The opening of the first element may have a smaller diameter than the base ring or flange. This may for example block the open end of the condom from going through the opening of the first element.

One or more embodiments may include a garment that is coupled directly or indirectly to the first user. The garment may have an interior surface facing the first user, and an exterior surface facing away from the first user. The exterior surface may have a hole. The first element and second element may couple releasably to a condom at the open and closed ends of the condom, respectively; both elements may couple directly or indirectly to the garment. When coupled to the second element, the closed end of the condom may be located on an inner portion, within, or on an outer portion of the garment. The first element may have a ring surrounding the hole, with a groove in the ring into which the base ring of the condom fits to couple the condom at the open end. The second element, which couples releasably to the closed end of the condom, may use various attachment mechanisms. These mechanisms may include for example: (i) a notch into which a small object placed at the closed of the condom fits, which holds the closed end since the notch is smaller than the small object; (ii) a button hole through which a small object placed at the closed of the condom fits; (iii) a loop that holds the closed end of a condom when the loop is cinched around the condom, and (iv) a surface that folds in two dimension, with a loop into which the closed end of the condom fits, and with a mechanism to hold a left portion and right portion of the surface together. The first and second elements may immobilize the open and closed ends of the condom relative to the first user when the second user moves a member in and out of the condom during non-penetrating sex. The apparatus may therefore ensure that the condom remains outside of all orifices of the first user, so that the sex is non-penetrating.

BRIEF DESCRIPTION OF THE DRAWINGS

The above and other aspects, features and advantages of the invention will be more apparent from the following more particular description thereof, presented in conjunction with the following drawings wherein:

FIG. 4G shows a top view of an illustrative button-type insert. FIG. 4H shows a side view of the button of FIG. 4G. FIG. 4I illustrates the button of FIG. 4G inserted into the closed end of a sheath, illustrated as a condom. FIG. 4J shows an illustrative embodiment of a button-hole type attachment mechanism. FIG. 4K shows a detailed side view of the closed end of a sheath, illustrated as a condom, temporarily attached to a garment or device using a button-type insert and a button-hole-type attachment mechanism.

FIG. 4L shows an illustrative notch-type mechanism. FIG. 4M shows an illustrative notch-type insert attachment mechanism manufactured in wire, and FIG. 4N shows the notch-type mechanism of FIG. 4M with a button-type insert. FIG. 4O shows a side view of an illustrative embodiment with a notch-type attachment mechanism and button-type insert, with the closed end of a sheath inserted and attached.

FIG. 4P shows a tapered element from one side perspective illustrating that the element has narrower and wider portions. FIG. 4Q illustrates another side of the tapered element that features an optional opening into an interior portion of the tapered element that extends from the narrower portion to the wider portion. FIG. 4Q also illustrates an area of attachment for coupling the tapered element to a garment or device. FIG. 4R illustrates the tapered element from a perspective looking down the length of the tapered element from the wider portion toward the narrower portion. FIG. 4S illustrates the same perspective as is illustrated in 4R, but with an insert element inserted into a closed end of a condom and positioned within the tapered element. FIG. 4T similarly illustrates the tapered element with an insert element inserted into the closed end of a condom and positioned within the tapered element, but from the side perspective illustrated in FIG. 4Q.

FIG. 7I shows the embodiment with a tubular element attached, and FIG. 7J shows the embodiment without a tubular element attached.

FIG. 7K shows the embodiment with a tubular element attached.

FIG. 7M shows the embodiment with a tubular element attached.

FIG. 7O shows the embodiment with a tubular element attached.

DETAILED DESCRIPTION OF THE INVENTION

An apparatus that enables non-penetrating sex will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1A:
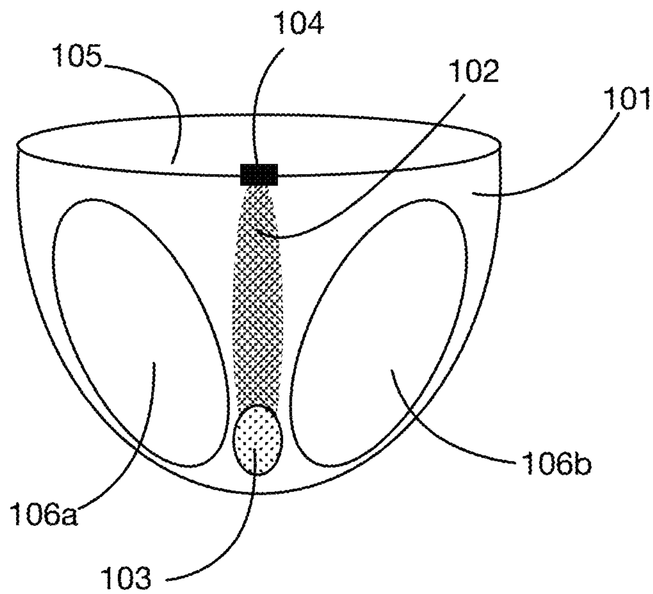
FIG. 1A illustrates a front view of embodiment of a device enabling "safe sex" with or without penetration and featuring "full coverage" of a first user.
Figure 1B:
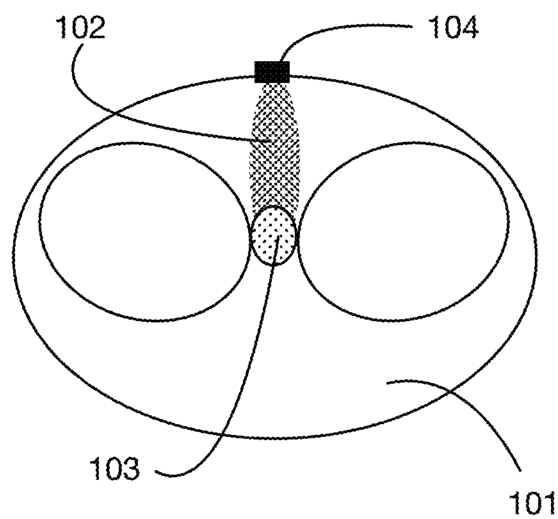
FIG. 1B shows a top view of the embodiment of FIG. 1A.
Figure 1C:
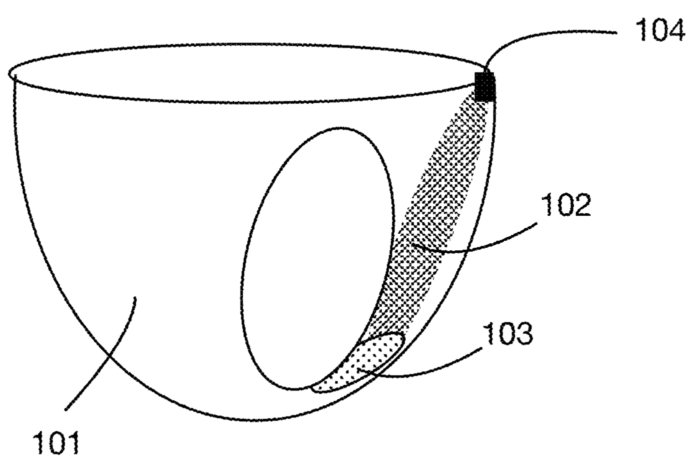
FIG. 1C shows a side view of the embodiment of FIG. 1A.

FIGS. 1A through 1C show an illustrative embodiment of a device that enables "safe sex" between a first user and a second user with or with penetration of the first user. FIG. 1A shows a front view, FIG. 1B shows a top view, and FIG. 1C shows a side view. The embodiment illustrated in FIG. 1A through 1C includes elements 101 enabling the device to be worn by a first user. (In some embodiments the first user may not wear a device and may for example control movement of a device attached to the second user.) In this example these elements are designed to resemble underwear or another similar garment, with openings 105 for the waist and 106*a* and 106*b* for the legs of a first user. In one or more embodiments, elements of the embodiment may be integrated into or attached to any garment. The term "garment" as used in this specification includes any item that may be worn by a user; a "garment" may include for example, without limitation, any conventional clothing or modification thereto, underwear, lingerie, a corset, pants, a dress, a skirt, a shirt, a jumpsuit, a waistband, a G-string, a belt, a panel that is worn by a user or attaches to a user or is inserted into another garment worn by the user, a string or strap or cord or ribbon that may be tied to the user or to another garment worn by the user, jewelry, and accessories. These elements may be constructed for example of a non-porous material, a porous material, a cloth, or a combination of materials. In one or more embodiments the material may be thin and/or degradable in quality over time, lending the device to be disposable. Certain types of natural or synthetic rubber (e.g., latex or nitrile) may lend themselves to such application, for example. Alternatively, the material may be robust enough to enable effective sanitization and re-use.

The embodiment illustrated in FIGS. 1A through 1C includes a tubular, sheath-like, or sleeve-like element 102 that is configured with an opening 103 on at least one end that enables insertion of a second user's penis into the tubular element. As illustrated in FIG. 1A, an opening 103 at one end of the tubular element 102 may open to the exterior of the device, exterior being the surface of the device facing away from the first user's body, and may for example be positioned between the first user's legs. A benefit of this type of configuration is that the insertion of a second user's penis and the movements of the two users may reflect body positions and motions that are broadly similar to those of common practice in penetrating coitus. A second benefit of this type of configuration is to enable insertion of the second user's penis and movement of the users to stimulate the exterior of the genitals and/or anus of the first user without penetration of the vagina or anus by the second user's penis.

As illustrated in FIG. 1A, the tubular element 102 may extend from the opening 103 positioned between the first user's legs upward to the portion of the device positioned near the first user's waist. FIGS. 1A through 1C illustrate a single tubular element 102 positioned in this way at the front side of the device. In one or more alternate embodiments, the device may be configured with a single tubular element positioned to extend from an opening between the first user's legs to a portion of the device near the first user's waist at the back side of the device. In one or more alternate embodiments, the device may be configured with multiple tubular elements, for example with one or more openings positioned between the first user's legs and one tubular element extending up the front side of the device and one tubular element extending up the back side of the device. These and other conceivable embodiments are within the scope of the invention.

In the example illustrated in FIGS. 1A through 1C the tubular element 102 is positioned between the body of the first user and material of the device that enables the device to be worn by a first user—the material configured to resemble underwear in the illustrated example. In this configuration the tubular element may be largely concealed by the portion of the device resembling underwear. An additional benefit of this configuration is that elastic tension between the first user's body and the portion of the device resembling underwear may provide an external source of compressive force on the tubular element. Such an external compressive force may enable compression-based stimulation of a second user's inserted penis that is greater than would be achieved with an independent tubular element of similar construction. This provides flexibility in the construction of the tubular element of the device, enabling, for example, use of materials that may not independently provide strong compressive stimulation of the inserted penis.

FIGS. 1A through 1C illustrate an attachment mechanism 104 connecting the upper end of tubular element 102—i.e., the end of the tubular element away from the opening into which a second user's penis may be inserted—near the waistband of the device 101. Such attachment may enable external stimulation of a first user's genitals or anus and stimulation of a second user's inserted penis without enabling penetration of the first user's genitals or anus by the second user's penis. Devices that lack an attachment of this end of the tubular element generally do not prevent penetration of the first user's body. The attachment mechanism may comprise for example a clip, strap, or other releasable mechanism, allowing the potential for release of the tubular element 102. Such a releasable attachment mechanism may, for example provide users with the option of either penetrating or non-penetrating sexual activity. Alternatively, the attachment mechanism 104 may comprise a permanent fixture of the device. For example, if the device is constructed as a single, molded piece of rubber, the upper end of the tubular element 102 may be molded onto the surface of the device positioned near the waist of the first user. This would prevent detachment of the tubular element without tearing or otherwise breaking the device. FIGS. 1A through 1C illustrate the attachment mechanism 104 with a single point of attachment at the waistband; however, in one or more embodiments the attachment mechanism may comprise one or more points of attachment along the tubular element 102 or may comprise a continuous attachment that extends the full length of the tubular element 102.

As described here, FIGS. 1A through 1C may alternatively represent configurations of the device with (i) a permanently attached tubular element, (ii) a detachable single or multi-use device with attachment mechanisms specifically designed for this purpose, or (iii) a detachable tubular element comprising either a conventional male condom or a conventional female condom.

Figure 2A:
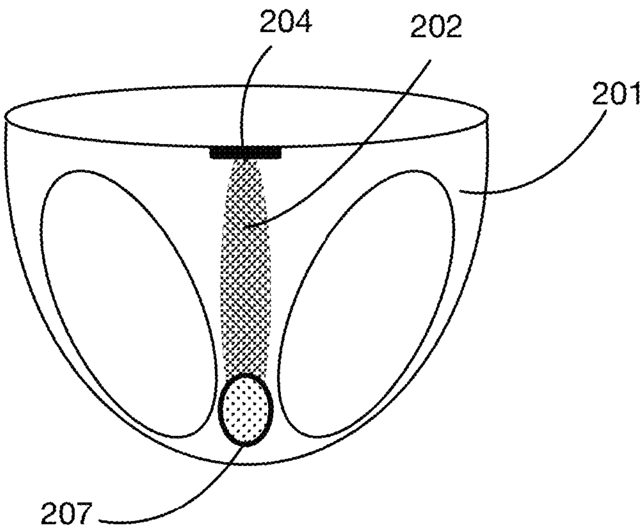
FIG. 2A illustrates a front view of an embodiment of a multi-use device affixed to or installed into garment enabling temporary attachment of single-use or multi-use sheath.
Figure 2B:
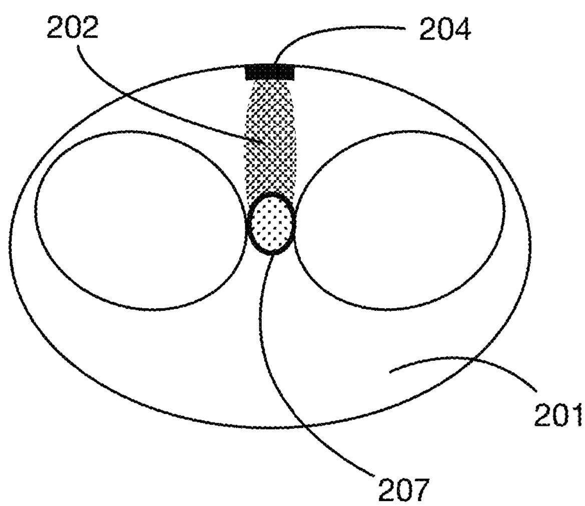
FIG. 2B shows a top view of the embodiment of FIG. 2A.
Figure 2C:
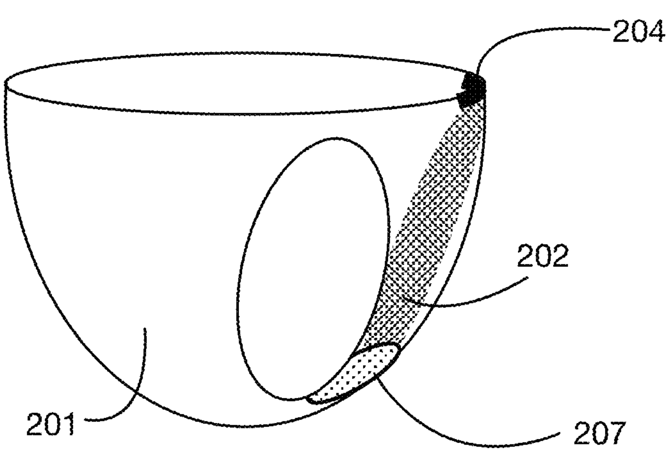
FIG. 2C shows a side view of the embodiment of FIG. 2A.

FIGS. 2A through 2C show an illustrative embodiment of the invention that comprises one or more attachment elements that enable temporary attachment of a detachable tubular, sheath-like, or sleeve-like device 202 to a device or garment 201 worn by a first user. FIG. 2A shows a front view, FIG. 2B shows a top view, and FIG. 2C shows a side view. The embodiment illustrated in FIGS. 2A through 2C is distinguished from the embodiment illustrated in FIGS. 1A through 1C in that the tubular element 202 is specifically detachable from the portion of the device 201 designed to resemble underwear or from a garment 201 onto which the attachment mechanisms are affixed.

Examples of a separately provided tubular element 202 that may be used in one or more embodiments include conventional condoms—of male or female types—and novel tubular elements that incorporate elements designed to enable their temporary attachment to the attachment elements. In embodiments where the tubular element comprises a conventional condom, the embodiments of the invention may comprise any or all of: the device(s) and/or elements enabling attachment of the condom; and the resulting system of devices that includes the condom and the devices and/or elements enabling its attachment. In embodiments where the tubular element comprises a novel device with elements specifically enabling temporary attachment to the attachment elements the invention may comprise any or all of: the device(s) and/or elements enabling attachment; the novel tubular element with elements enabling attachment; and the system of devices that include the device(s) and or elements enabling attachment and the novel tubular element with elements enabling attachment.

The terms "male condom" or "male-type" in reference to a conventional condom means a condom that is configured to be positioned on a male member and to have a stationary position with respect to the male member during sexual activity. The term male member may refer to a penis or other type of body part that is typically inserted into or otherwise penetrates a portion of a receiving person's body during penetrative sex. Male condoms are generally held in place on the male member by a combination of elastic compression around the circumference of the male member and friction against that member created by the elastic compression. The compressive force and friction are generally increased by the presence of a base ring, or thickened portion of the condom material, around the opening of the male condom. The dimensions of male condoms vary substantially; however, a typical male condom may measure eight (8) inches in length and one-and-a-half (1.5) inches in diameter at the base ring.

The measurements of male condoms have significant implications for the configuration and relative positioning of attachment mechanisms illustrated in FIGS. 2A through 2C and referenced elsewhere herein where the device is configured for use with a conventional male condom. For example, in order to avoid excess movement in the tubular element 202 with respect to the first user's body, where the device is configured for use with a male-type condom, the distance between an attachment mechanism of a closed end of a condom 204 may be positioned approximately 8 inches away from the furthest portion of an attachment mechanism of an open end of a condom 207. This length may be shortened to account for any lengths of the tubular element that are taken up by the attachment mechanism to provide secure attachment of the open and closed ends of the condom. For example, if the attachment mechanisms for the open and closed ends of the condom reduce the effective length of the condom by one quarter (0.25) inches combined, then the distance between these two mechanisms may be reduced from 8 inches to seven-and-three-quarters (7.75) inches. Attachment mechanisms that minimize the length of the condom that is required to be used in providing secure attachment of the open or closed ends of the condom may therefore provide more usable length for the condom when attached.

The distance between the elements specified here is illustrative, as the dimensions of male condoms can vary and because the elastic nature of male condoms allows for some variance in the relative positions of attachment mechanisms without compromising the functionality of the device. The preferred distance between the attachment mechanisms may also be affected by consideration of the expected curvature of the material and/or the curvature of the external surface of the first user's body between the two attachment mechanisms and by potential impacts on the comfort of the users. Increasing the distance will tend to increase the tension across the length of the condom, which may increase compression of a male member inserted within the condom and may increase the pressure and concentration of pressure of the condom against the first user's body. Given the sensitivity typical of affected portions of the first user's body, there may be tradeoffs with respect to this pressure in defining the optimal spacing between the attachment mechanisms. As a result of these various factors, the distance between the positions of the attachment mechanisms 204 and 207 in one or more embodiments configured for use with a conventional male condom may range between six (6) inches and nine (9) inches, for example.

The terms "female condom" and "female type" in reference to a condom means a condom that is configured to be positioned inside the vagina, anus, or other body cavity of a first user and to have a stationary position relative to the first user's body during sexual activity. The closed end of a female condom is typically positioned inside the first user's body cavity and held in position using a ring that is inserted into the closed end of the tubular element and that is configured to put outward pressure on the interior walls of the body cavity. To ensure that the outward pressure created by the ring insert is sufficient to secure the closed end of the female condom inside the body cavity, the ring insert of a conventional female condom is typically greater than or equal to two (2) inches in diameter. The open end of a female condom is typically positioned on the outside of a first user's body orifice that opens into the body cavity in which the condom is positioned. Female condoms generally incorporate a base ring at the open end of the tubular element that is both sufficiently wide and sufficiently rigid to prevent the open end of the condom from being pulled inside the body orifice of the first user during sexual activity. In order to accomplish this, the base ring on a female condom is typically greater than two-and-a-half (2.5) inches in diameter. Tension between the base ring secured against the outside of the first user's body orifice to the body cavity at the open end of the condom and the ring insert secured against the interior surface of the body cavity at the closed end of the condom end is generally sufficient to hold the female condom in a stationary position with respect to the first user's body during sexual activity. The length of conventional female condoms—from the closed end to the open end—can vary, but a typical or representative length may be seven (7) inches when the ring insert is not inserted into the condom. Positioning the ring insert into the closed end of the female condom can substantially reduce the operable length of the tubular element from 7 inches down to five-and-a-half inches, for example. In practice, the operable length may be further reduced by the portion of the tubular element that remains outside the first user's body orifice and spans the distance across the external surface of the first user's body between the opening of the body orifice and the base ring on the female condom.

The measurements and configuration of conventional female condoms may affect the configuration and relative positioning of attachment mechanisms illustrated in FIGS. 2A through 2C and referenced elsewhere herein where the device is configured for use with conventional female condoms. For example, in order to avoid excess movement in the tubular element 202 with respect to the first user's body, where the device is configured for use with a female-type condom, the distance between an attachment mechanism of a closed end of a condom 204 may be positioned approximately 7 inches away from the furthest portion of an attachment mechanism of an open end of a condom 207. This length may be shortened to account for any lengths of the tubular element that are taken up by the attachment mechanisms used to provide secure attachment of the open and closed ends of the condom. For example, if the attachment mechanisms for the open and closed ends of the condom reduce the effective length of the condom by 0.25 inches combined, then the distance between these two mechanisms may be reduced from 7 inches to six-and-three-quarters (6.75) inches. Attachment mechanisms that minimize the length of a female condom that is required to be used in providing secure attachment of the open or closed ends of the condom may therefore provide more usable length for the condom when attached.

As with the discussion of the distances between attachment mechanisms in configurations intended for use with male condom type tubular elements, the distance between the elements specified here is illustrative, as the dimensions of female condoms can vary and because, while the elasticity of female condoms may be less than that of male condoms, their elasticity does allow for some variance in the relative positions of attachment mechanisms without compromising the functionality of the device. The distance between the attachment mechanisms may also be affected by consideration of the expected curvature of the material and/or the curvature of the external surface of the first user's body between the two attachment mechanisms and by potential impacts on the comfort of the users. Increasing the distance will tend to increase the tension across the length of the condom, which may increase compression of a male member inserted within the condom and may increase the pressure and concentration of pressure of the condom against the first user's body. Given the sensitivity typical of affected portions of the first user's body, there may be tradeoffs with respect to this pressure in defining the optimal spacing between the attachment mechanisms. As a result of these various factors, the distance between the positions of the attachment mechanisms 204 and 207 in one or more embodiments configured for use with a conventional female condom may range between four (4) inches and eight (8) inches, for example.

As illustrated in FIGS. 2A through 2C, elements enabling temporary attachment of a separately provided tubular device 202 may include a mechanism 207 enabling attachment of an open end of the tubular device 202. In this example, the separately-provided tubular device 202 may be a conventional condom and the attachment mechanism 207 at the open end of the condom may be a ring-type attachment mechanism, an illustrative embodiment of which is described below with respect to FIGS. 3A through 3C.

The elements enabling temporary attachment may also include a mechanism 204 enabling temporary attachment of a closed end of the tubular device 202. Such mechanisms may include one or more straps, clips, loops, or other mechanisms to attach the closed end of the condom or areas at various points along the tubular device to the device or a garment 201. In the example illustrated in FIGS. 2A through 2C the attachment mechanism 204 for the closed end of the condom may be for example a loop-and-fold type mechanism, an illustrative embodiment of which is described below with respect to FIGS. 4A through 4F. As noted above, such attachment mechanism(s) can substantially prevent or otherwise limit the ability of a penis or member of the second user that is inserted into the tubular element from penetrating the vagina, anus, or other body part of the first user.

In one or more embodiments, other types of attachment mechanisms may be used for the open end or the closed end of a tubular device. Examples may include for example, but are not limited to, sleeves, pouches, button holes, slots, notches, hooks or straps that may be sewn into a garment.

In one or more embodiments, the elements enabling temporary attachment of a detachable or separately provided tubular device, illustrated in FIGS. 2A through 2C as a conventional condom, may be either temporarily or permanently affixed to: a single-use device worn by a first user; a multi-use device worn by a first user; a garment worn by a first user; or a single or multi-use device enabling a first user to have at least partial control over the position and/or movement of the detachable tubular element, into which a second user's penis may be inserted.

Figure 3A:
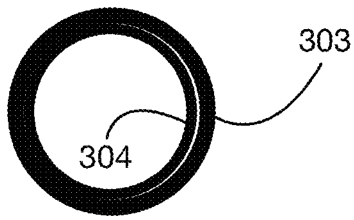
FIG. 3A illustrates a front view of an embodiment of a ring-type mechanism for temporary attachment of the open end of single or multi-use sheath, such as a conventional male or female condom.
Figure 3B:
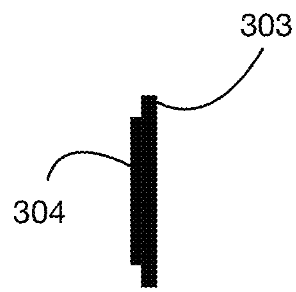
FIG. 3B shows a side view of the embodiment of FIG. 3A.
Figure 3C:
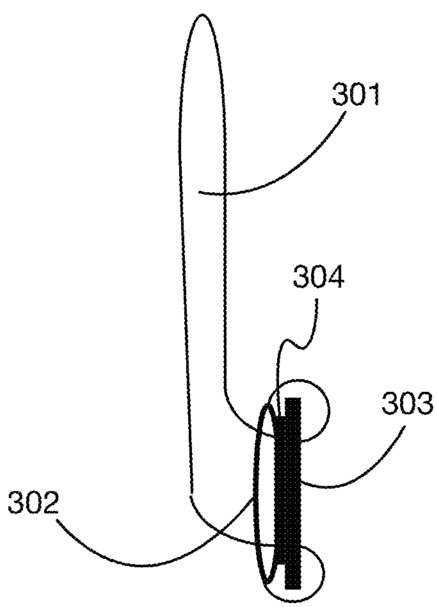
FIG. 3C shows a side view of the embodiment of FIG. 3A with a single-use sheath inserted.

FIGS. 3A through 3C show an illustrative embodiment of a ring-type attachment mechanism that enables temporary attachment of the open end of a detachable and/or separately provided sheath or tubular device. The tubular device 301 illustrated in FIG. 3C may be for example a conventional condom. Other types of attachment mechanisms for the open end of a detachable device, including other types of ring-type mechanisms, and other types of detachable tubular devices are conceivable within the scope of the invention. FIGS. 3A and 3B provide front and side views of the ring-type attachment mechanism, respectively. FIG. 3C provides a side view of the ring-type attachment mechanism with a condom 301 attached.

The example ring-type attachment mechanism illustrated in FIGS. 3A through 3C may comprise a ring with at least a portion 303 that has a diameter larger than the diameter of the condom 301 at the condom's opening. As illustrated in FIG. 3C, the condom 301 may be attached by inserting the closed end and length of the condom through the ring-type mechanism and by stretching the open end of the condom, wrapping or folding the open end of the condom back over the ring-type attachment device, and releasing the open end so it fits securely against the ring-type mechanism. The elastic nature of conventional condoms, compressive force provided by the stretched condom, and friction between the condom and the ring-type device may contribute to providing a secure connection between the condom and the ring-type attachment mechanism.

In order to enhance the security of attachment, the ring-type attachment device may have a portion 304 positioned toward the closed end of the condom 301 that has is relatively smaller diameter and a portion 303 positioned away from the closed end of the condom that has a relatively larger diameter. This is illustrated in FIGS. 3B and 3C. As illustrated in FIG. 3C, when the open end of the condom is stretched and folded back over the ring-type attachment mechanism, the "base ring" 302 of the condom—a thicker portion of the condom that is typically positioned at the opening of conventional condoms—may be released so that it sits behind the larger diameter portion 303 of the ring-type mechanism. The relatively higher compressive force exerted by the stretched base ring of the condom and the position of the base ring behind the larger diameter portion 303 of the ring-type attachment mechanism, combined with the friction between the condom and the ring-type attachment mechanism, may limit the ability of the base ring 302 and the condom 301 to inadvertently slide off of or detach from the ring-type attachment device. The ring-type attachment may be made out of a plastic or elastomer material for example an elastomeric material and may have a ramp feature between 0 and 90 degrees on the outer and/or inner edges to provide a more comfortable attachment than a rigid attachment for example.

As noted above, the diameter of male-type condoms varies, but a typical diameter of a male condom base ring may be 1.5 inches. In this case, and given the highly elastic nature of male-type condoms, including the base ring of male-type condoms, the relatively larger diameter portion 303 of the ring-type mechanism configured for use with a male-type condom may range from 1.5 inches in diameter to over three (3) inches in diameter. Sizing of the ring-type attachment mechanisms configured for use with male-type condoms may vary in order to optimize the device's performance with respect to various factors, including the desired security of attachment, the ranges in diameter of various male-type condoms, the fragility of male-type condoms, and the comfort of the users, for example. Optimization across these factors may further reflect the specific design of the ring-type mechanism, including its shape and construction material(s), for example.

FIGS. 3D through 3F and FIGS. 3G through 3I illustrate two additional embodiments for the ring-type attachment mechanism illustrated in FIGS. 3A through 3C. Specifically, a potential issue with the ring-type mechanism illustrated in FIG. 3A through 3C is that it may be challenging to size appropriately for any width penis. In this context, it may also be challenging to select an optimal material. In some use cases, the ring may be either (a) too firm to stretch around a wider-than-anticipated penis, or too floppy to hold up against the compression created by the base ring of the condom. The embodiments shown in FIG. 3D-3F and 3G-3I address this issue with a mechanism that is similar to a bracelet that expands to stretch around a person's hand, which uses beads strung along an elastic thread. The beads prevent the bracelet from collapsing below a certain diameter, but the elastic between the beads allows the bracelet to stretch over a hand.

Figure 3D:
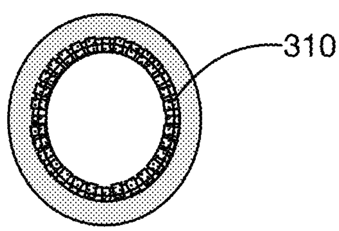
FIG. 3D shows an embodiment of a beaded ring-type mechanism for temporary attachment of the open end of single or multi-use sheath, which may comprise for example a conventional male or female condom.
Figure 3E:
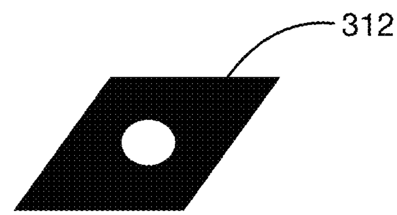
FIG. 3E shows a detailed view of a bead in the embodiment of FIG. 3D.
Figure 3F:
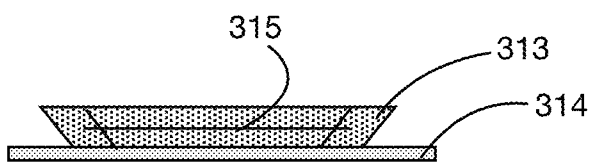
FIG. 3F shows a side view of the bead of FIG. 3E.

FIG. 3D illustrates a top view of an embodiment of a ring-type attachment mechanism that comprises a circle of beads 310 on an elastic thread (and possibly encased in an elastomer material) with a base flange 314 to enable the beaded ring to attach to a device. FIG. 3E shows a side view of a single bead 312. FIG. 3F shows a side view of this bead, illustrating bead profile 313, base flange 314, and an optional elastic thread 315. In this illustrative embodiment the beads have an angled profile. This angled profile may for example provide a funnel shape for an entering penis or other member of the second user.

Figure 3G:
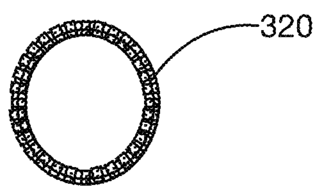
FIG. 3G shows another embodiment of a beaded ring-type mechanism for temporary attachment of the open end of single or multi-use sheath, with a different bead configuration.
Figure 3H:
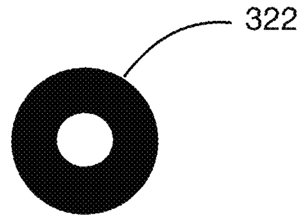
FIG. 3H shows a detailed view of a bead in the embodiment of FIG. 3G.
Figure 3I:
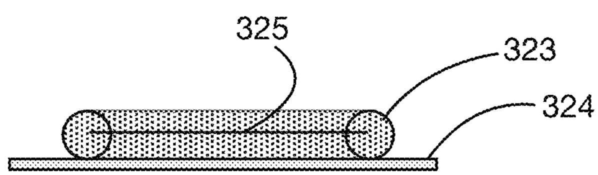
FIG. 3I shows a side view of the bead of FIG. 3H.

FIG. 3G illustrates a top view of an embodiment of a ring-type attachment mechanism that comprises a circle of beads 320 on an elastic thread with a base flange to enable the beaded ring to attach to a device. FIG. 3H shows a side view of a single bead 322. FIG. 3I shows a side view of this bead, illustrating bead profile 323, base flange 324, and an optional elastic thread 325. In this illustrative embodiment the beads have a round profile.

Figure 3J:
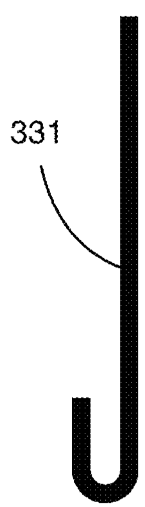
FIG. 3J shows an illustrative embodiment of a partial ring or hook-type attachment mechanism for temporary attachment of an open end of a single or multi-use sheath to a garment or control device.
Figure 3K:
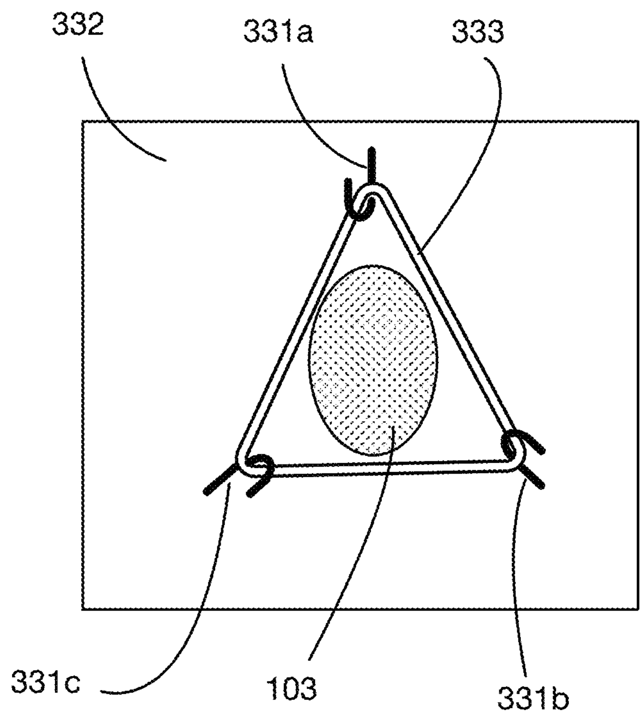
FIG. 3K shows an illustrative embodiment with three hooks located around the opening in a garment or device to secure the base ring of a condom or other tubular element.

FIG. 3J shows an embodiment of a partial ring or hook-type attachment mechanism for temporary attachment of an open end of a single or multi-use sheath to a garment or control device. One or more hooks like hook 331 shown in FIG. 3J may for example be positioned in a few locations around the opening to collectively hold the base ring of a condom open. FIG. 3K illustrates an embodiment with three hooks 331*a*, 331*b*, and 331*c* positioned like corners of a triangle around opening 103 in material 332. The base ring 333 of a condom may stretch and fit securely over these three hooks. In one or more embodiments, a hook-type mechanism may effectively substitute for a ring-type mechanism such as one illustrated in FIGS. 3A-3C. A benefit of this arrangement is that the stretchy material of the panel or flange (between the hooks) may allow the tubular element to stretch freely around any size penis or other member of the second user and provide relatively greater freedom of movement than an attachment mechanism comprising a complete ring around the opening.

Figure 4A:
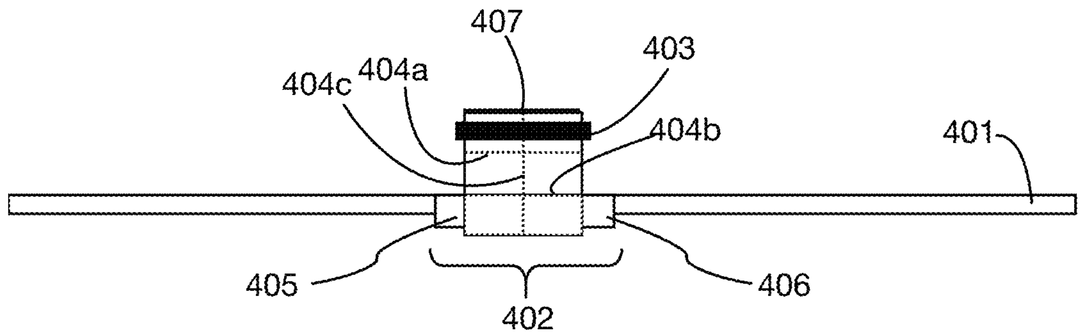
FIG. 4A shows an illustrative embodiment of a loop-&-fold type mechanism for temporary attachment of the closed end of single-use or multi-use sheath.

FIGS. 4A through 4F illustrate an embodiment of a loop-and-fold type mechanism for temporarily attaching a closed end of a single or multi-use sheath-like or tubular element. FIG. 4A illustrates elements of the attachment mechanism 402 in a position on the waistband 401 of a device or garment that may be worn by a first user. In this example, the loop-and-fold mechanism 402 comprises: a rectangular piece of material 407 configured to enable folding in two dimensions, in this embodiment along fold lines 404*a*, 404*b*, and 404*c*; a strap or ribbon of material 403 forming a loop across one end of the rectangular piece of material 407; a point of attachment to a waistband 401 or any other portion of a garment or device that may be worn by a first user or attached to a first user and/or at least partially controlled by a first user; and a fastening system enabling one side of the rectangular material to be fastened across the other side of the rectangular material once it has been folded. On section 405 of the rectangular material, the side facing away from the waistband may for example have a hook-&-loop system (e.g., a VELCRO® brand fastener) or other system enabling temporary fastening to the other side of the mechanism. On section 406, the side that is facing the waistband 401 may be affixed to the waistband. The side facing away from the waistband may for example have a hook-&-loop system (e.g., a VELCRO® brand fastener) or other system enabling temporary fastening of the other side of the mechanism.

The strap or ribbon 403 may be attached to the rectangular material 407 on both ends to form a loop across the rectangular position. This loop may be positioned at the top of the rectangular material. The point of attachment to a waistband 401 of a garment may be positioned for example in the bottom, right side of the rectangular material 407. This portion may be permanently affixed to the waistband (e.g., using thread to sew the material onto the waistband) or may be temporarily affixed to the waistband using a hook-and-loop fastening system like VELCRO® or another type of temporary fastening system (e.g., hooks, loops, straps, clips, buttons, etc.). This (bottom right) portion of the rectangular material may also have a temporary fastening system (e.g., hook-and-loop type fastening system like VELCRO®) that enables the left side 405 of the rectangular material to be temporarily fastened across the right side 406 of the rectangular material after it is folded.

Figure 4B:
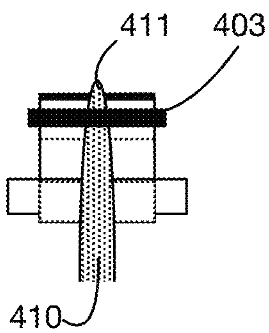
FIGS. 4B, 4C, 4D, and 4E show illustrative steps in inserting a condom into the mechanism and folding it to secure it.
Figure 4C:
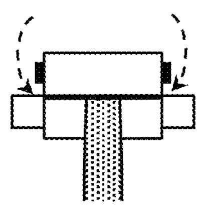
Figure 4D:
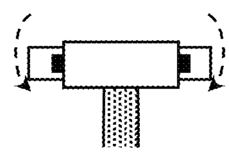
Figure 4E:
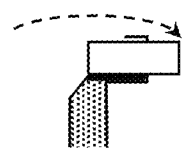

FIGS. 4B through 4E show an illustrative progression of steps to temporarily attach the closed end of a condom 410 in the loop-and-fold type device 402 shown in FIG. 4A. Arrows with dashed lines are used in the illustration to indicate movements of the mechanism that define the progression of steps to attach the condom 410. As illustrated in FIG. 4B, the closed tip 411 of the condom 410 may be inserted under the loop created by the ribbon or strap 403 that is attached across the rectangular material. As illustrated in FIG. 4C, the rectangular material may then be folded down over the loop 403 with the closed end of the condom, such that the fold is perpendicular to the length of the condom sheath, along fold line 404*a* in FIG. 4A, to create a first fold. As illustrated in FIG. 4D, the rectangular material may then be folded down a second time perpendicular to the length of the condom sheath to form a second fold along fold line 404*b* in FIG. 4A. This may be repeated one or more additional times, according to various designs, embodiments, and implementations of the mechanism. In one or more embodiments, rolling of the material may be also used instead of or in addition to differentiated folds. The folds perpendicular to the length of the condom sheath may create friction sufficient to prevent the closed end of the condom from sliding out of the loop and inadvertently detaching from the device.

As illustrated in 4E again the folded or rolled rectangular material may be folded across from left to right with a fold that is parallel to the length of the condom sheath, along fold line 404*c* in FIG. 4A. This fold is perpendicular to the initial folds (or rolls) and may prevent the material from unfolding inadvertently and releasing the closed end of the condom. As illustrated, this final fold may be secured using a hook-and-loop type fastening system, or other fastening system, to fasten the side of the rectangular material that is not connected to the waistband (the left side 405 of the rectangular material, as illustrated in FIG. 4A) to the side 406 of the rectangular material that is affixed to the waistband (the right side of the rectangular material, as illustrated in FIG. 4A).

Figure 4F:
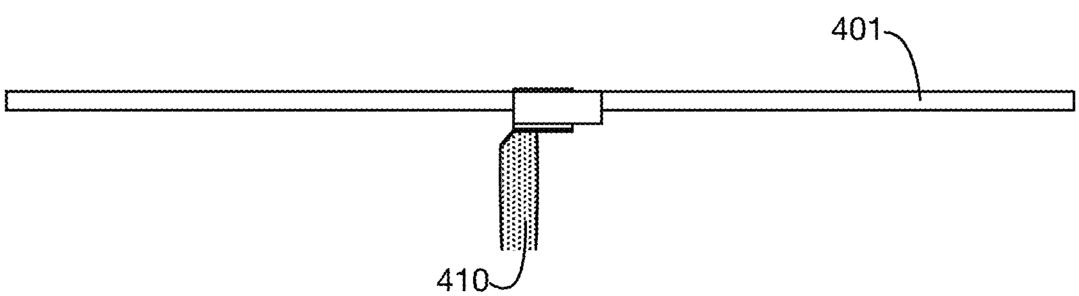
FIG. 4F shows an illustrative embodiment of a loop-&-fold type mechanism with the closed end of a condom temporarily attached to a waistband of a device or of a garment worn by a first user.

FIG. 4F illustrates the result of inserting the closed end of the condom 410 under the loop, folding the rectangular material perpendicular to and then parallel to the length of the condom sheath, and fastening the loose side of the mechanism to the right side, which is affixed to the garment waistband 401. This result is that the example loop-and-fold mechanism illustrated in FIG. 4A provides a means of temporarily attaching the closed end of the condom or other detachable sheath (whether a single use or sanitize-able multi-use sheath) to the waistband of a garment, to another area of a garment, to a device that may be worn by a first user, or to a device that may otherwise enable a first user to have at least partial control of the position or movement of the sheath.

In some embodiments, the functioning of a loop-and-fold type attachment mechanism may be enhanced, with respect to the security of attachment or the simplicity of folds, for example, by incorporating an insert-type mechanism inside the closed end of the tubular element, as illustrated in FIGS. 4G through 4O. This and other related variants of a loop-and-fold type mechanism are not separately illustrated, but are within the scope of the invention.

Figure 4G:
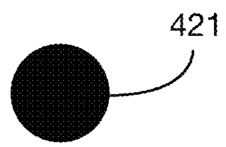
FIGS. 4G through 4K illustrate an embodiment with an insert-type mechanism, illustrated with a button-type insert and button-hole-type attachment mechanism, for temporary attachment of the closed end of a single or multi-use sheath to a garment or other device.
Figure 4H:
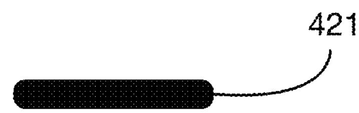
Figure 4I:
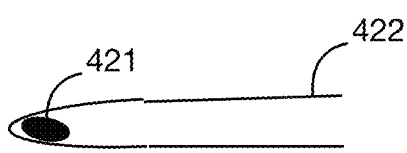
Figure 4J:
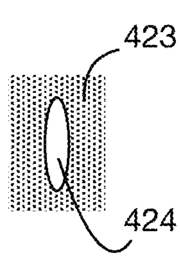
Figure 4K:
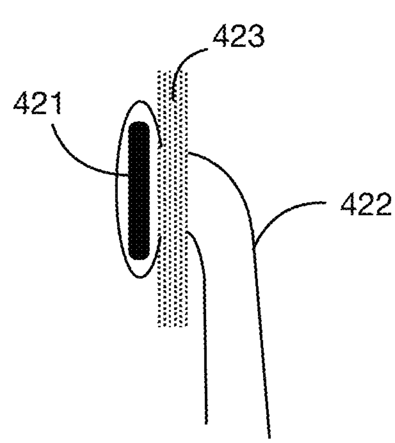

FIG. 4G through 4K show an illustrative embodiment with an insert-type mechanism for temporary attachment of the closed end of a condom or other sheath to a garment or other device. An insert-type mechanism for attaching the closed end may for example require insertion of an insert into the condom or sheath, and placing the insert at or near the closed end of the condom. The insert may then fit through one or more securing elements that hold it in place. FIGS. 4G and 4H show an illustrative embodiment of an insert, which may for example be a button or a similar shape item. FIG. 4G shows a top view of insert 421, and FIG. 4H shows a side view of insert 421. FIG. 4I shows insert 421 inserted into condom 422 and placed at the closed end of the condom. FIG. 4J shows an illustrative embodiment of an attachment device into which the closed end of the condom 422 fits along with the insert 421. For a button-type insert similar to insert 421, the attachment device may be for example a button hole 424 in material 423. Material 423 may for example be part of a pair of underwear or may be another part of the device. The hole 424 may be configured for the button-type insert 421 to pass through and catch behind. Condom 422 may for example be secured by inserting the insert 421 into the condom, as shown in FIG. 4I, and passing the button insert 421 through the button hole 424. FIG. 4K shows a side view of condom 422 inserted through button hole 424 in material 423 and held in place by the button-type insert 421.

Figure 4L:
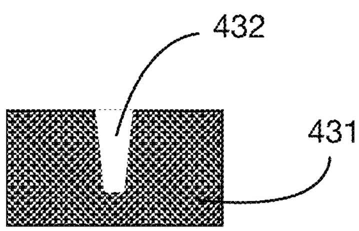
FIG. 4L through 4O illustrate an embodiment with an insert-type mechanism, illustrated with a button-type insert and notch-type attachment mechanisms, for temporary attachment of the closed end of a single or multi-use sheath to a garment or other device.

FIG. 4L shows an illustrative embodiment with a slot-type or notch-type mechanism that may be used for example to secure a condom or other sheath with a button insert similar to the insert shown in FIGS. 4G and 4H. In some situations it may be easier or faster for a user, for example, to slide a button into a slot or notch made from a material with a relatively firm structure than it would be to place a button through a button-hole. In the embodiment shown in FIG. 4L, material 431 has notch 432, which may for example have a width at the bottom end of the notch that is smaller than the width or diameter of the button-type insert. Material 432 may for example be a firm material that will hold the button in position once it is inserted behind the notch.

Figure 4M:
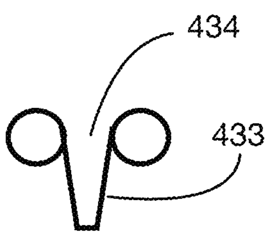
Figure 4N:
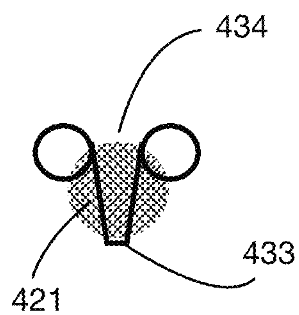
Figure 4O:
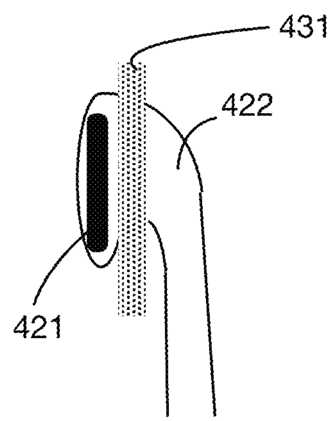

FIGS. 4M and 4N illustrate another embodiment of a slot-type or notch-type mechanism. FIG. 4M shows a notch-type mechanism that may be made for example from wire or hard plastic 433. Notch 434 is formed between two arms of the material 433. This is similar to the shape used for "hook-&-eye" fasteners used in women's dresses, bras, etc.; however, in this case, a button inserted into a condom or other tubular element is positioned into the slot instead of a conventional hook. FIG. 4N shows the notch mechanism of FIG. 4M with a button-type insert 421 secured behind the mechanism. FIG. 4O shows a side view of a condom 422 with its closed end secured into material 431 containing a notch, with the button-type insert 421 inserted into the condom and slipped into a notch in the material. The notch may for example be a notch similar to notch 432 or similar to notch 434. One or more embodiments may use any type of notch or slot made from any type of material or combination of materials to secure an insert in a condom at the closed end of the condom.

A potential advantage of the insert-type mechanisms illustrated in FIGS. 4G through 4O and referenced elsewhere herein is the relatively small size of inserts that may be used. This may be particularly relevant in comparison to the ring inserts used with conventional female condoms. As noted above, the ring insert in a typical female condom may be 2 to 2.5 inches in diameter. The relatively large size of these ring inserts is inherent to their proper functioning because they much be large enough to exert sufficient outward pressure against the inside surface of a first user's body cavity to secure the position of the closed end of the female condom inside the body cavity. However, inserting such a large element into a closed end of a condom can substantially reduce the condom's operational length. In contrast, the button-type insert mechanisms illustrated in FIGS. 4G through 4O and referenced elsewhere herein can be configured to be less than one half (0.5) inch in diameter. Using an insert mechanism of this relatively small size means that a much smaller amount of the condom length is required to provide a secure attachment. The ability to effectively extend the functional length of a tubular element by using such a small insert provides a potential advantage for the ability of the device to satisfy users with various sizes of anatomy and more generally to improve the enjoyment of sexual activities.

Note that while FIGS. 4G through 4O illustrate an insert mechanism with a round, button-like shape, insert mechanisms with other shapes are conceivable and fall within the scope of the invention. Examples include for example inserts with the shape of a ball, ring, triangle, hook, bar, or other similar shape. Such alternate shapes may be particularly well suited for other types of corresponding attachment mechanisms attached to or through the balance of the device. For example, ball, ring, or disk-shaped insert mechanisms may be configured to fit into a snap-type device. Hook shaped insert mechanisms may be configured to fit into an eye-type attachment mechanism, for example. Ring-shaped insert mechanisms may be configured to fit into a hook-type attachment mechanism, for example. Insert mechanisms with triangular, trapezoidal, diamond, round, ball or other similar shapes may be configured to fit into a mechanism that is shaped in part like a flattened funnel, for example. Insert mechanisms shaped like a ball, bar, or tube, may be configured to fit into a slider, sleeve, or partial sleeve-type mechanism, for example. All of these and similar type insert mechanisms are within the scope of the invention.

Other shapes of insert may also be used to attach a closed end of a condom or other type of tubular element within the scope of the invention. For example, the insert may comprise a ring and the mechanism attached to the material 431 may comprise a hook, snap, or other mechanism that securely attaches to the ring with the condom material held in between the insert and the attachment mechanism.

Affixing an attachment mechanism for the open end of a condom or detachable sheath and another attachment mechanism for the other end of a condom or detachable sheath to a garment or device may provide a means of temporarily attaching a detachable and/or separately provided condom, sheath, or other tubular element to the garment or device in such a way that the penis or other member of a second user may be inserted into the tubular element without being inserted into the vagina, anus, or other body cavity of a first user. The attachment mechanism for the open end may for example be a ring-type mechanism, a hook-type mechanism, or any other mechanism that holds the open end of the condom securely against the garment or device. The attachment mechanism for the closed end may be for example a loop-and-fold type mechanism, or a mechanism such as a button hole or notch that may be used with an insert into the condom. As a result, these mechanisms provide illustrative examples of elements that may be incorporated into one or more embodiments such as the embodiment illustrated in FIG. 2A. These mechanisms are illustrative examples, only, however; other mechanisms may be incorporated into one or more embodiments to provide a similar function within the scope of the invention.

Figure 4P:
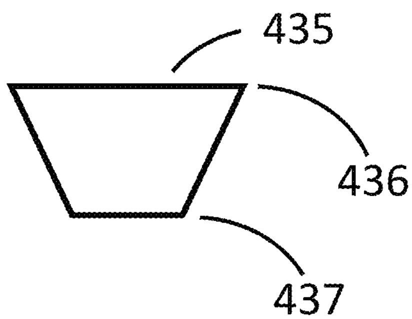
FIGS. 4P through 4T show an illustrative embodiment of a tapered insert attachment mechanism.
Figure 4Q:
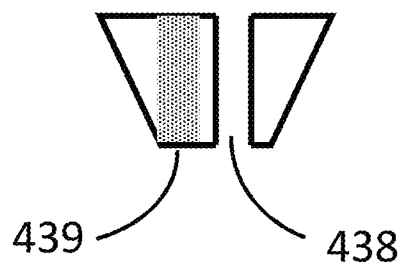
Figure 4R:
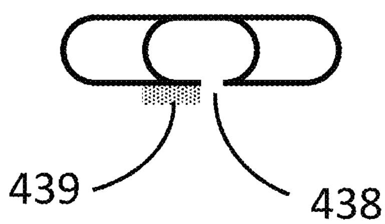
Figure 4T:
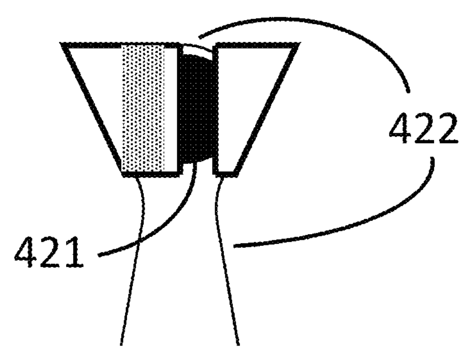
Figure 4S:
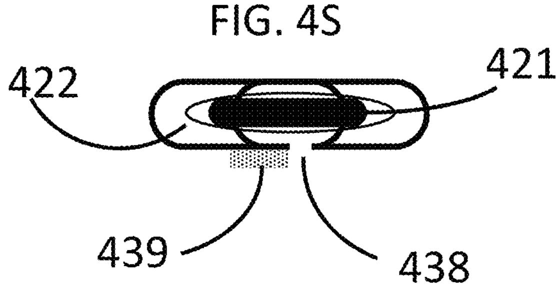

FIGS. 4P through 4T illustrate another example of an attachment mechanism for a closed end of a tubular element or condom comprising an element 435 with a tapered shape similar in some respects to a funnel or flattened funnel. FIG. 4P illustrates an example of such an attachment mechanism 435. The element may comprise a wider portion 436 that is oriented to be facing away from the attachment point for the open end of the condom or tubular element and a narrower portion 437 that is oriented to be facing toward the attachment point for the open end of the condom or tubular element. The wider portion 436 may be configured to be at least as wide as, or wider than, the width of an insert-type element that may be inserted into the closed end of a condom or tubular element, while the narrower portion 437 may be configured to be narrower than or at least as narrow as the width of an insert-type element that may be inserted into a closed end of a condom or tubular element. In this way, an insert-type element inserted inside a closed end of a condom or tubular element can pass into the wider portion 436 of the tapered element 435, but cannot pass out of the narrower portion 437 of the tapered element 435. FIG. 4P illustrates the example attachment element from the perspective of one side, which may be the side oriented either toward or away from the surface of the garment or device to which the attachment element is coupled, for example. FIG. 4Q illustrates the same attachment mechanism from the perspective of another side. The side illustrated in 4Q features an optional opening 438 that extends from an outside portion of the tapered element 435 to an inside portion of the tapered element 435, the opening spanning the length of the tapered element 435 from the wider portion 436 to the narrower portion 437. The purpose of this opening is to simplify the coupling of the attachment element 435 to a condom or tubular element 422 when an insert element 421 inserted into the closed end of the condom or tubular element. Specifically, this type of configuration enables the length of the condom 422 to pass through the opening 438 and into the inside portion of the tapered element 435 while the closed end of the condom 422 is on the side of the tapered element 435 with the wider portion 436 and while the open end of the condom is on the side of the tapered element 435 with the narrower portion 437. FIG. 4Q also illustrates an area of attachment 439 where the tapered attachment element 435 may be coupled to a surface of a garment or device when the side with an opening 438 is facing the surface of the coupled garment or device. FIG. 4R illustrates the tapered attachment element 435 from the perspective of the end with the wider portion 436, and viewing down through the interior portion of the tapered element 435 toward the end with the narrower portion 437. FIG. 4R also illustrates the opening 438 on one side of the tapered element, and illustrates an area of attachment 439 where the tapered element 435 may be coupled to a garment or device. In this example the area of attachment 439 is on the same side of the tapered element 435 as the opening 438. FIG. 4S illustrates the same view of the tapered element 435 as is illustrated in FIG. 4R, but with an insert element 421 inserted into the closed end of a condom 422 and positioned within the inside portion of the tapered element. FIG. 4T illustrates the same view of the tapered element 435 as is illustrated in FIG. 4Q, but with an insert element 421 inserted into the closed end of a condom 422 and positioned within the inside portion of the tapered element. As illustrated here, the insert element 421 inserted into the closed end of the condom 422 is narrow enough to fit through the wide portion 436 of the tapered element 435, but is too wide to fit through the narrow portion 437 of the tapered element 435. As a result, the tapered element 435 provides for secure attachment of the closed end of a condom or tubular element 422 when an insert element 421 is inserted into the closed end of the condom or tubular element 422. FIG. 4T also makes it clear how the opening 438 can allow the length of the condom or tubular element 422 to be passed into an interior portion of the tapered element 435 while an insert element 421 is inserted into the closed end of the condom is positioned on the side of the tapered element 435 with the wider portion 436 and while the open end of the condom is positioned on the side the tapered element 435 with the narrower portion 437.

More generally, the attachment mechanisms described above, or other mechanisms providing similar function, may be integrated with a device that may be worn by a first user. They may be permanently affixed to a garment that may be worn by a first user, or they may be configured to enable temporary attachment of the mechanisms to a garment worn by a first user.

In one or more embodiments, a ring-type attachment mechanism may be permanently installed (e.g., sewn with thread) onto the outside of a garment, such that the tubular element may extend along the outside of the garment (outside meaning the side of the garment facing away from the first user's body). With this configuration, the ring-type element may for example be connected to the garment only on the side of the ring opposite the direction that the tubular element will extend (e.g., away from the waistband). This may enable a second user's penis to enter the device through the ring and penetrate a tubular element lying along the outside of the garment without enabling the penis to penetrate the first user's vagina, anus, or other body part. A potential benefit of this configuration is to reduce the extent of alterations to the garment (e.g., to avoid creating additional openings in the garment).

Alternatively, in one or more embodiments a ring-type attachment mechanism may be permanently installed (e.g., using thread stitching) to an opening in the garment (e.g., positioned between the leg openings in the garment), such that the tubular element may extend along the inside of the garment ("inside" meaning the side of the garment facing toward the first user's body), similar to the position of the tubular element illustrated in FIGS. 1A and 2A. Alternatively, the opening in the garment may penetrate one or more layers of the garment, but not all layers of the garment, such that one or more layers of the garment act as a liner to further prevent penetration of the first user's body.

In one or more embodiments, attachment mechanisms similar to those described above may alternatively be temporarily affixed to a garment, for example using clips, straps, loop-and-hook type fastening, adhesives, or other fastening systems. For example, the attachment mechanisms may be affixed to a material with adhesive backing capable of temporarily adhering onto the surface of a garment or device. In such cases, the fastening systems may connect the ring-type attachment mechanism to the garment on one side of the ring, for example on the side opposite the direction that the tubular element is intended to extend. This may enable a second user's penis to enter the device through the ring and penetrate a tubular element that extends along the exterior of the garment or device without enabling the penis to penetrate the first user's vagina, anus, or other body part.

Figure 5A:
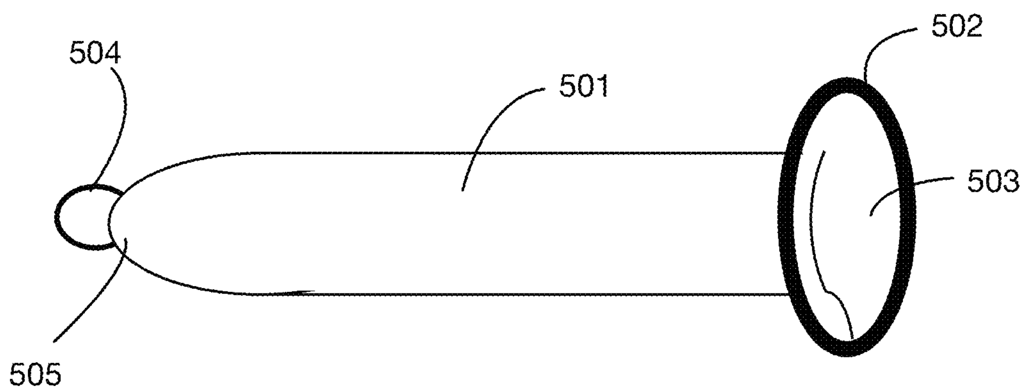
FIG. 5A illustrates an embodiment with a sheath-like or tubular device with elements enabling temporary attachment to attachment mechanisms affixed to a garment or device.
Figure 5B:
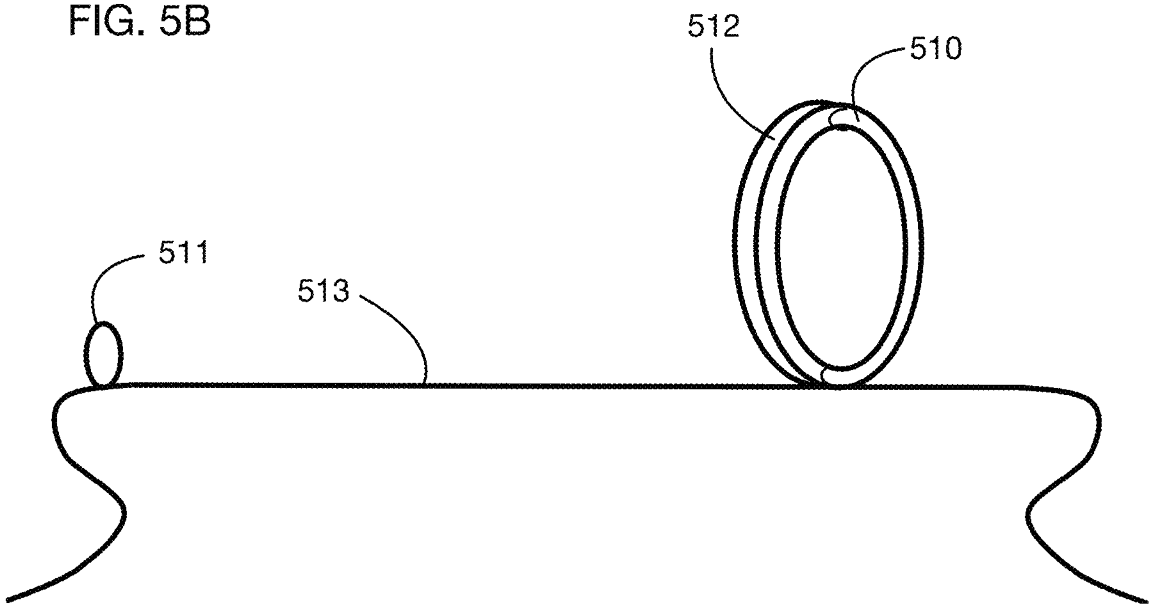
FIG. 5B shows an illustrative attachment mechanism that may be used to attach the sheath of FIG. 5A.

The illustrations and discussion provided above with respect to FIGS. 2A through 2C, 3A through 3K, and 4A through 4O all reflect the potential to temporarily attach a detachable or separately provided tubular element or sheath, which may for example be in the form of a conventional condom or may be in the form of a novel tubular element specifically configured to attach to the device. FIGS. 5A and 5B illustrate an embodiment with a novel tubular device (i.e., other than a conventional condom) that incorporates elements to specifically enable temporary attachment of the tubular device to another garment or device via attachment mechanisms affixed to the other garment or device. FIG. 5A illustrates the tubular device. FIG. 5B illustrates the attachment mechanisms affixed to another garment or device.

The illustrative embodiment of a tubular device 501 shown in FIG. 5A features a firm base ring 502 integrated with an open end 503 that is configured to enable insertion of a user's penis. It also features a loop 504 integrated at a closed end 505 of the sheath.

The illustrative embodiment of an attachment mechanism shown in FIG. 5B features a ring-type attachment mechanism 510 on the right side and a loop-type attachment mechanism 511 on the left side. The ring-type attachment mechanism 510 may have a groove or channel 512 that is configured to reflect the size and shape of the firm base ring 502 at the open end of the tubular device 501. More specifically, the groove or channel 512 may be configured so that it makes a ring with a diameter similar to the diameter of the firm base ring 502. It may be further configured with an opening that is slightly narrower than the width of the firm base ring 502 and with a more open space behind the opening of the groove or channel 512 (i.e., further inside the ring-type mechanism). This may allow the firm base ring 502 of the tubular device to enter the channel or groove 512 only when a specific force is applied around the circumference of the firm base ring. As a result, the open end 503 of the tubular device may be securely attached to the ring-type attachment mechanism 510 by pressing the firm base ring 502 into the groove or channel 512. The open end 503 of the tubular device may also be removed by applying sufficient force to pull the firm base ring out of the groove or channel.

The force required to insert the firm base ring 502 of the tubular element 501 into the channel or groove 512 of the ring-type attachment mechanism 510 may be adjusted for example by adjusting the relative size of the firm base ring and the opening to the channel or groove. Similarly, the force required to remove the firm base ring 502 of the tubular element from the channel or groove 512 of the ring-type attachment mechanism 510 may be adjusted by adjusting the relative size of the firm base ring and the opening to the channel or groove. In this way, by adjusting the relative sizes of the channel or groove opening 512 and the firm base ring 502 of the tubular element 501, the mechanisms may be configured to provide a secure, temporary attachment of the tubular device 501 to the ring-type attachment mechanism 510.

In various embodiments the firm base ring 502 may be configured with a firmness greater than, less then, or similar to the firmness of a conventional condom. In some embodiments, the ring-type attachment mechanism 512 may be configured with segments that provide security of attachment while other segments are relatively more elastic to ensure freedom of movement and comfort for the users. Such embodiments are analogous to the segmented ring or hook-type configurations discussed with respect to FIGS. 3J through 3K, for example.

Attachment of the closed end 504 of the tubular device 501 may be accomplished for example by connecting the loop 504 that is integrated with the tubular device to the loop-type attachment mechanism 511. One way to form this connection is to feed the loop 504 that is integrated with the tubular device through the loop-type attachment mechanism 511, stretch open the loop 504 that is integrated with the tubular device 501, and then feed the sheath-portion of the tubular device (including the firm base ring) through the loop that has been fed through the loop-type attachment mechanism 511. After this end is connected, the sheath may be extended down to the ring-type attachment mechanism 510, the firm base ring 502 may be squeezed through the opening in the ring-type attachment mechanism 510, and finally the firm base ring 502 may be snapped into the groove 512 to secure the firm base ring to the ring-type attachment mechanism. Many other types of mechanisms may similarly provide for attachment of the loop-type mechanism 504 on a tubular element 501 to a device or garment 513, including but not limited to hooks, clips, or straps, for example.

These and similar elements and devices may be configured in a variety of ways to achieve similar function within the scope of the invention. For example, in one or more embodiments a tubular element may have openings and firm base rings at both ends rather than having one open end and one closed end. Alternatively, in one or more embodiments the attachment mechanisms may incorporate or comprise various combinations of straps, hooks, loops, clips, or other mechanisms. In the embodiment shown in FIG. 5B, the loop-type attachment mechanism 511 and the ring-type attachment mechanism 510 are coupled to item 513, which may for example be any or all of a strap, a ribbon, another mechanism enabling at least partial control of the device by a first user, a surface of a portion of a device worn by a first user, or a surface of a garment worn by a first user onto which attachment mechanisms are affixed. These or other attachment mechanisms may be permanently or temporarily affixed to various garments or devices that may be worn by a first user or may otherwise enable at least partial control of position and/or movement of the tubular element.

Figures 6A, 6B, 6C:
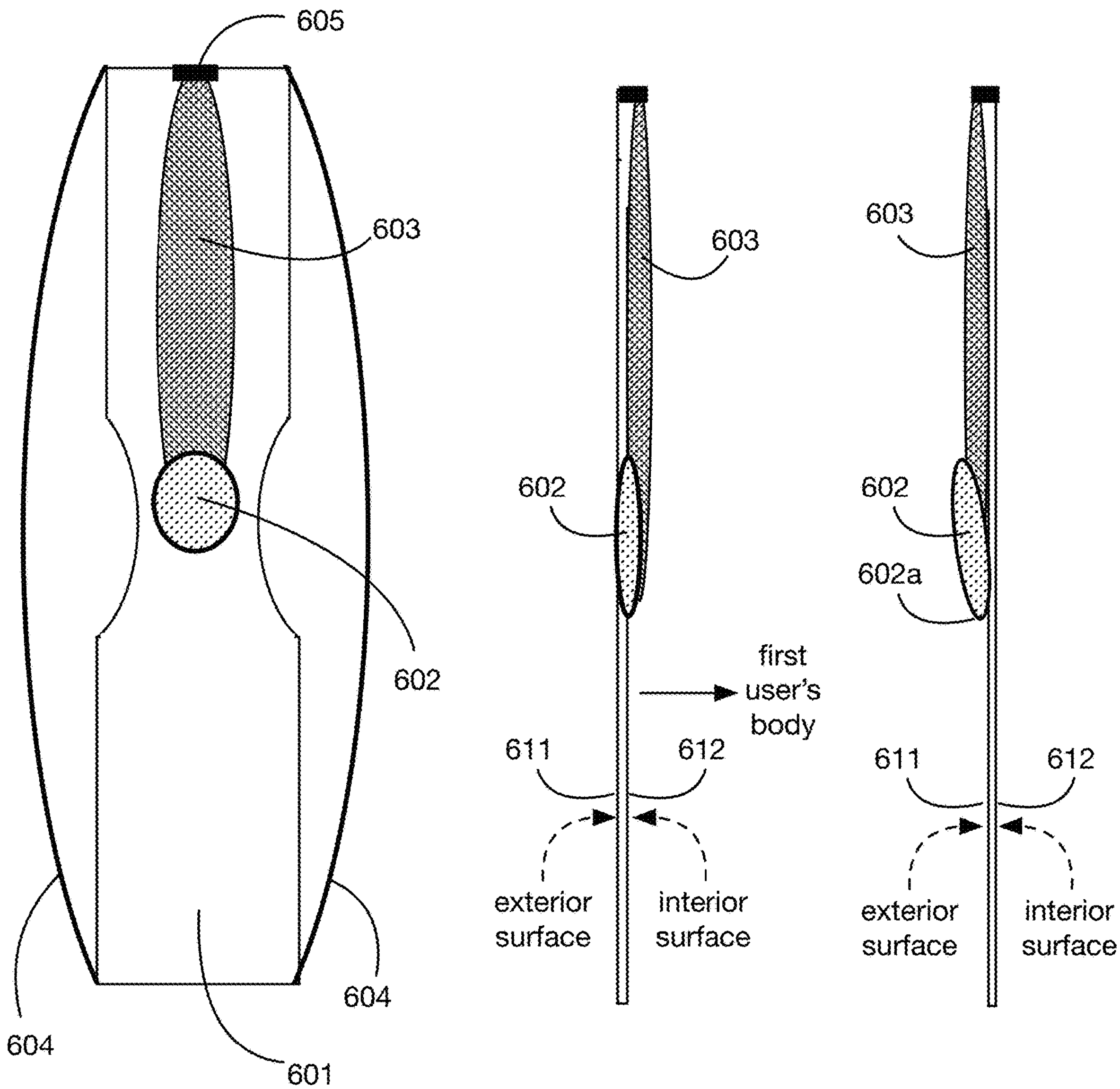
FIG. 6A shows a top view of an illustrative embodiment of a single-use device, multi-use device or garment, or multi-use device or garment with attached single-use sheath that enables "safe sex" with or without penetration, featuring "limited coverage" of the first user.
FIG. 6B shows a side view of the embodiment of FIG. 6A with the sheath interior to the device or garment.
FIG. 6C shows a side view of the embodiment of FIG. 6A with the sheath exterior to the device or garment.
Figure 7A:
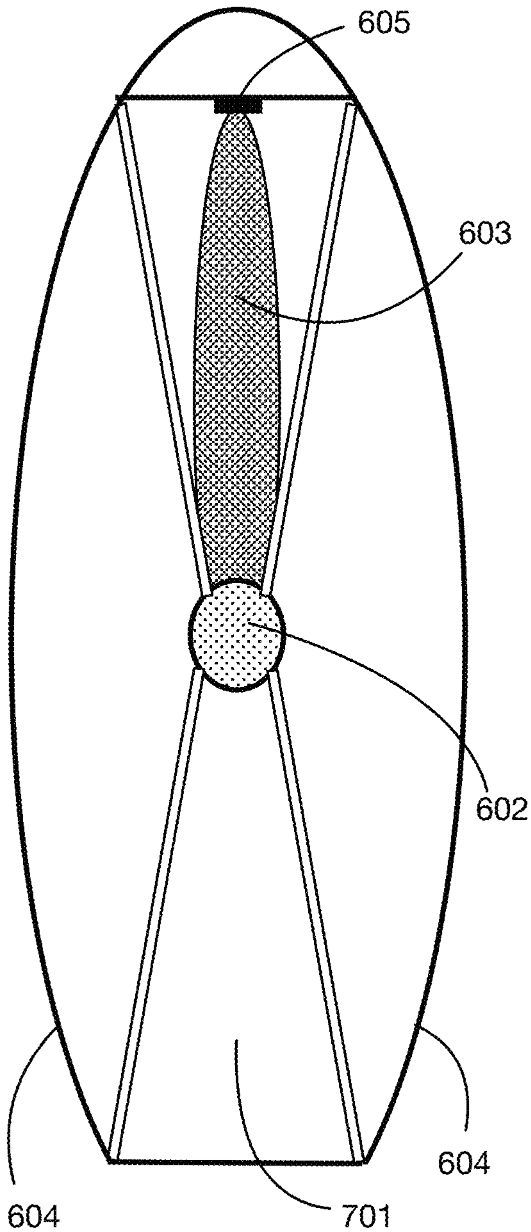
FIG. 7A shows a top view of another illustrative embodiment of a single-use device, multi-use device or garment, or multi-use device or garment with attached single-use sheath that enables "safe sex" with or without penetration, featuring "limited coverage" of the first user.
Figure 7B:
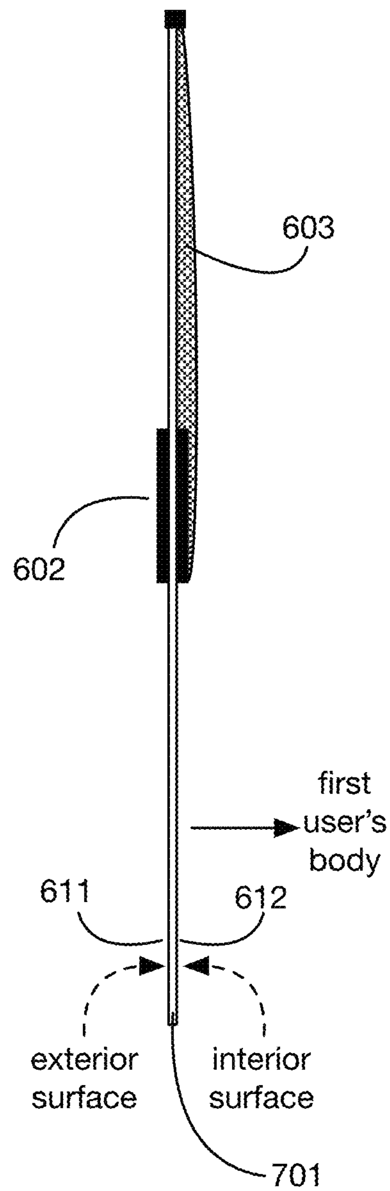
FIG. 7B shows a side view of the embodiment of FIG. 7A with the sheath interior to the device or garment.

FIGS. 6A through 6C and 7A and 7B illustrate examples of embodiments like those illustrated in FIGS. 1A through 1C and 2A through 2C, in which the device or garment that may be worn by a first user provides relatively less coverage of the first user's body than is provided in the examples illustrated in FIGS. 1A through 1C and 2A through 2C. In particular, the embodiments illustrated in FIGS. 6A through 6C provide an intermediate level of coverage for the body of the first user, while the embodiments illustrated in FIGS. 7A and 7B provide no substantive coverage of the body of the first user that is wearing the device.

The embodiment illustrated in FIG. 6A, shown as a top view, features material 601 that extends between the legs of the first user, from the front of the waistband 604 to the back. This material includes an opening 602 positioned between the legs of the first user. The opening 602 may connect directly to the open end of an integrated tubular element 603 that may be configured to enable insertion of a second user's penis. Alternatively, the opening 602 may incorporate a ring-type or other attachment mechanism enabling temporary attachment of a detachable or separately provided tubular device. In one or more embodiments the waistband 604 and/or the material 601 extending between a first user's legs may include an attachment mechanism at one or more other points of the tubular element in addition to an attachment mechanism at the opening. For example, one or more embodiments may have an attachment mechanism like mechanism 605 to connect the closed end of a tubular element 603 to the waistband 604 and/or the material 601. One or more embodiments may have one or more attachment mechanisms connecting the length of the tubular element to the material and/or waistband. These attachment mechanisms may comprise a permanent or temporary means of attaching to the tubular element. In one or more embodiments the integrated waistband 604 may be replaced with or supplemented with clips or another mechanism enabling the device to be temporarily attached to underwear or another garment worn by the first user or to a belt, strap, or string fitted around the waist or another portion of the first user's body.

FIG. 6B illustrates a variation of the embodiment of FIG. 6A, shown as a side view, where the tubular element 603 is configured so as to be positioned between the first user's body and an interior surface 612 of one or more elements enabling the device to be worn by the first user. In such embodiments the opening 602 at the end of the tubular element 603 may extend from the interior of the tubular element to the exterior surface 611 of the device, thereby enabling the penis of a second user to be inserted into the tubular element. In such configurations, the opening of the tubular element may for example be connected (directly or indirectly via a ring-type attachment mechanism) around the full circumference of the opening to the material extending between the first user's legs. Such embodiments benefit from compressive force provided by the material 601 against the tubular element and the first user's body. Among other benefits, this enables the tubular element to be manufactured from a particularly thin material and places the body parts of the two users in particularly close proximity. These structural aspects of the configuration illustrated in FIG. 6B serve to further enhance the stimulation and transmission of sensations between the users for their mutual benefit.

As an alternative, FIG. 6C illustrates an embodiment where the tubular element 603 is configured so as to be positioned on the exterior surface 611 of the device, shown as a side view. In one or more embodiments, the opening of the tubular element may be connected (directly or indirectly via a ring-type attachment mechanism) to the material extending between the first user's legs for only a portion of its circumference. For example, it may be connected only on the side 602*a* of the opening 602 opposite the direction that the tubular element extends along the outside 611 of the material. A potential advantage of this type of configuration is that it may require minimal alteration to a garment or other device enabling the device to be worn by a first user—because the ring and tubular element are all on the exterior.

FIG. 7A illustrates another embodiment that provides limited coverage of the first user, shown as a top view. This embodiment may for example be similar to the embodiments illustrated in FIGS. 6A through 6C, with a different shape of the material 701 to provide more limited or different coverage of the first user. FIG. 7B shows a side view of a variation on the embodiment of FIG. 7A with the tubular element 603 on the interior of the device, between the interior surface 612 and the first user's body. One or more embodiments may provide a variation of the embodiment of FIG. 7A with the tubular element on the exterior of the device, as in FIG. 6C for example. A benefit of the example embodiment illustrated in 7A and 7B, and other similar embodiments, is that it may be compatible for use with a variety of garments that have one or more holes in them, but that don't have the mechanisms required to attach a tubular element.

Like embodiments of the invention configured according to the examples illustrated in FIGS. 1A through 1C and 2A through 2C, embodiments configured to provide relatively less body coverage for the first user, as illustrated in FIGS. 6A through 6C and 7A and 7B, may alternately be worn directly against a first user's body, worn over one or more garments, including conventional underwear, for example, or may be worn such that the tubular element passes through an opening in a garment. This may be enabled for example by the waistbands that are included in these examples. Similar embodiments may be configured without a waistband, substituting other mechanisms to enable attachment, directly or indirectly, to a garment or another device. This could be accomplished, for example, by integrating various types of attachment or fastening mechanisms to the points of the device that connect to the waistbands illustrated in FIGS. 6A and 7A. Such fastening mechanisms may include for example one or more hooks, clips, straps, adhesive elements, hook-and-loop type fastening systems, buttons, or other available fastening systems, or any combination thereof.

More generally, one or more embodiments may comprise a device or system of devices that may be temporarily attached to the exterior of a garment worn by a first user. In such embodiments, the presence of a garment between the device and the first user's body may enable insertion of a second user's penis into the tubular element without enabling penetration of the vagina, anus, or other body part of the first user. Such embodiments may for example comprise one or more devices or a system of devices with elements providing for attachment to a first user's garment and one or more tubular, sheath-like, or sleeve-like elements that are open on at least one end and configured to enable insertion of a second user's penis into the tubular element. The element or elements providing for attachment to a garment may include one or more clips, straps, or adhesives, for example. Garments worn by a first user, to which such devices may be attached may include, but are not limited to, underwear, leggings, shorts, or pants, or other similar garments, for example.

In one or more embodiments the tubular element may be configured so that when the device is attached to a garment the tubular element is exposed on the exterior of the garment and may come into direct contact with a second user. In other embodiments, the tubular element may be configured so that it is positioned between the garment worn by a first user and another layer of material of the device, which may be positioned between the tubular element and the first user's body. In such embodiments, this layer of material may provide a compressive force to the tubular element. A potential benefit of such a configuration may be to increase the compressive force applied to a penis inserted into the tubular element, thereby increasing stimulation of the penis, without requiring the tubular element to be manufactured in a way that independently increases its compressive characteristics.

Figure 7C:
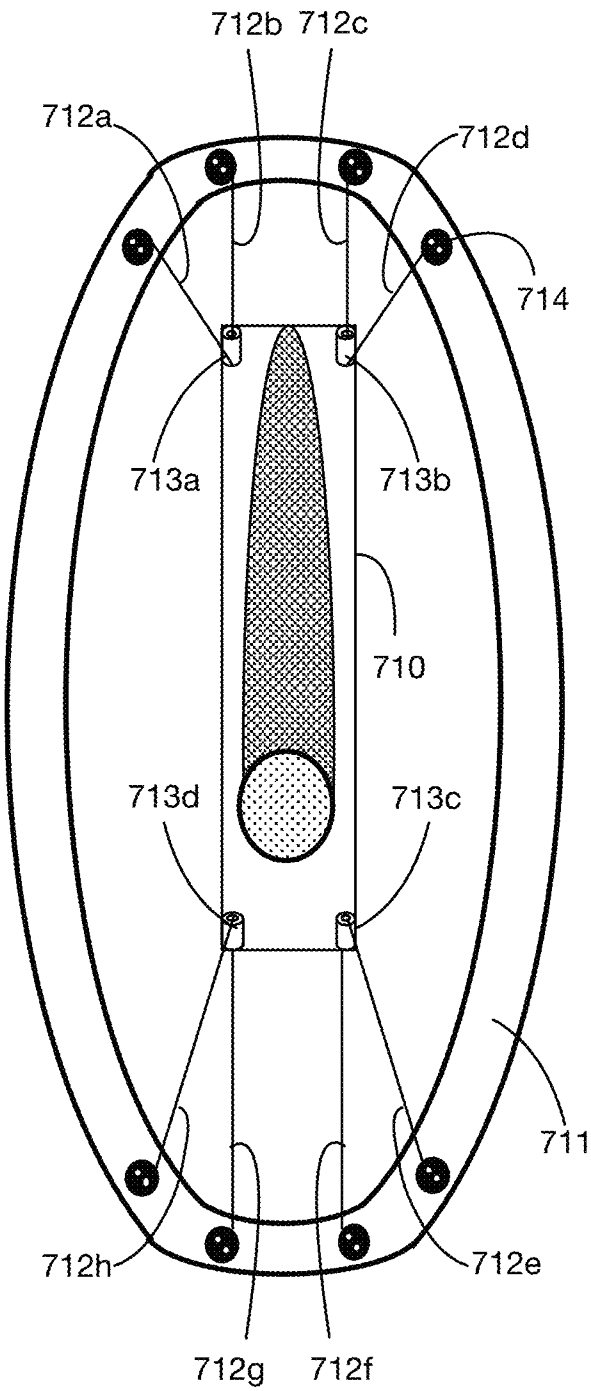
FIG. 7C shows a top view of an illustrative embodiment of a single-use device, multi-use device or garment, or multi-use device or garment with attached single-use sheath that enables "safe sex" with or without penetration, featuring control lines that attach the single-use sheath to the waistband.
Figure 7D:
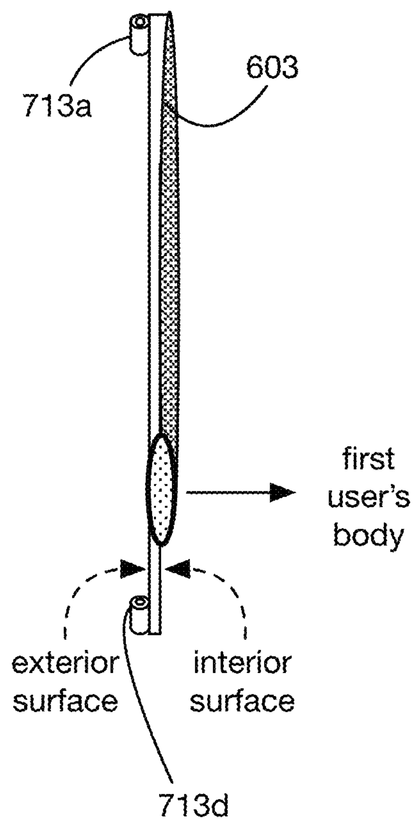
FIG. 7D shows a side view of the embodiment of FIG. 7C with the sheath interior to the device or garment.

FIGS. 7C and 7D illustrate a top view and side view, respectively, of an embodiment enabling attachment of the device 710 to a waistband 711. The term waistband may include for example, without limitation, a conventional waistband, a belt, fabric or string worn around the waist, or any similar mechanism. In the embodiment shown, strings 712*a* through 712*h* run from waistband 711 through loops or hooks 713*a* through 713*d* that are attached to the device 710, and back to the waistband 711. The ends of the strings may be secured at the waistband for example by wrapping the string around a button, such as button 714 shown in FIG. 7C for attachment of string 712*d*, similar for example to the way old-fashioned letters are closed by wrapping a string around two cardboard buttons, or with snaps or similar mechanisms. Potential benefits of this arrangement may include for example that each corner of the device 710 is secured along three axes and the position of the device is fully adjustable. In one or more embodiments the waistband 711 may be configured to be used multiple times, for example with a single-use replaceable device 710. The waistband 711 may be fitted with clips, buttons, and/or other mechanisms to enable control cords connected to a single or multi-use component with a tubular element. Alternatively, the multi-use waistband may be fitted with control cords that can be temporarily affixed to the single or multi-use component with a tubular element using clips, hooks, and/or other similar mechanisms. The multi-use waistband may be a standalone component or may be integrated with garments or other components or devices worn or controlled by a user. One or more embodiments similar to that of FIG. 7C may have either a fully integrated tubular element or a tubular element (e.g., single use condom) that may be temporarily attached. FIG. 7D shows a side view of a variation of the embodiment of FIG. 7C where the tubular element 603 is on the interior of the device, between the interior surface and the first user's body. Such configurations may benefit from the compressive force generated by the material 710 against the first users body, the ability to use tubular elements comprised of a thin material that does not provide substantial independent compressive force, and the close proximity between the user's body parts to enhance their mutual stimulation and the transmission of sensations between them. Alternatively, one or more variations of the embodiment of FIG. 7C may locate tubular element 603 on the exterior, similar to the embodiment shown in FIG. 6C.

Figure 7E:
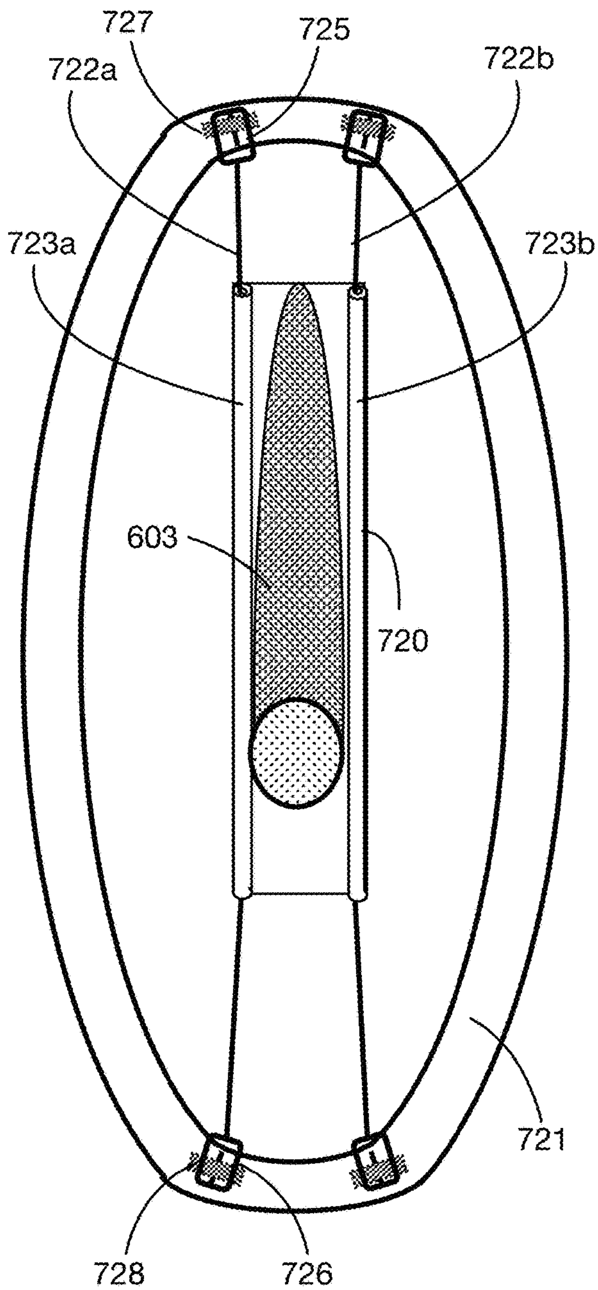
FIG. 7E shows a top view of another illustrative embodiment of a single-use device, multi-use device or garment, or multi-use device or garment with attached single-use sheath that enables "safe sex" with or without penetration, featuring control lines that attach the single-use sheath to the waistband using clips.
Figure 7F:
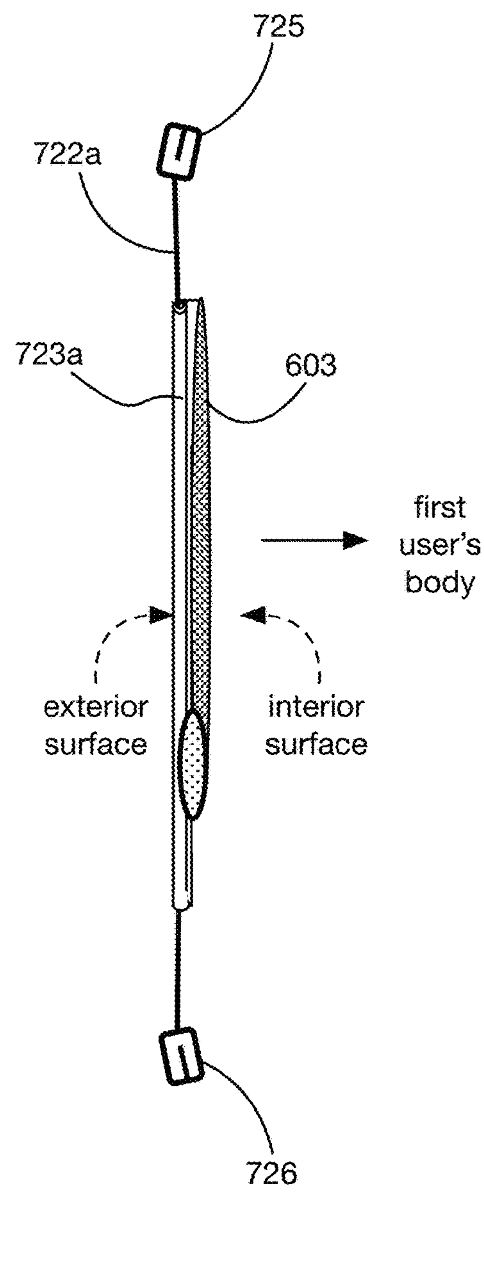
FIG. 7F shows a side view of the embodiment of FIG. 7E with the sheath interior to the device or garment.

FIGS. 7E and 7F illustrate another embodiment that enables attachment of the device 720 to a waistband 721. FIG. 7E shows a top view, and FIG. 7F shows a side view of an embodiment with the tubular element 603 on the interior of the device. (In one or more embodiments the tubular element may be located on the exterior of the device.) In this embodiment, strings 722*a* and 722*b* run through channels or tubes 723*a* and 723*b* along the sides of the device 720. The strings may for example have hooks or clips on each end, which may for example hook onto loops in the waistband (or simply over the top of the waistband). In one or more embodiments any type of attachment mechanism may be used to attach the strings 722*a* and 722*b* to the waistband 721. For example, string 722*a* has attached clips 725 and 726, which clip over loops 727 and 728, respectively, in waistband 721. A potential benefit of this arrangement is that the position of the device may be adjusted along the length of the strings. In one or more embodiments the device may have a fully integrated tubular element; in one or more embodiments a tubular element (e.g., single use condom) may be temporarily attached.

Figure 7G:
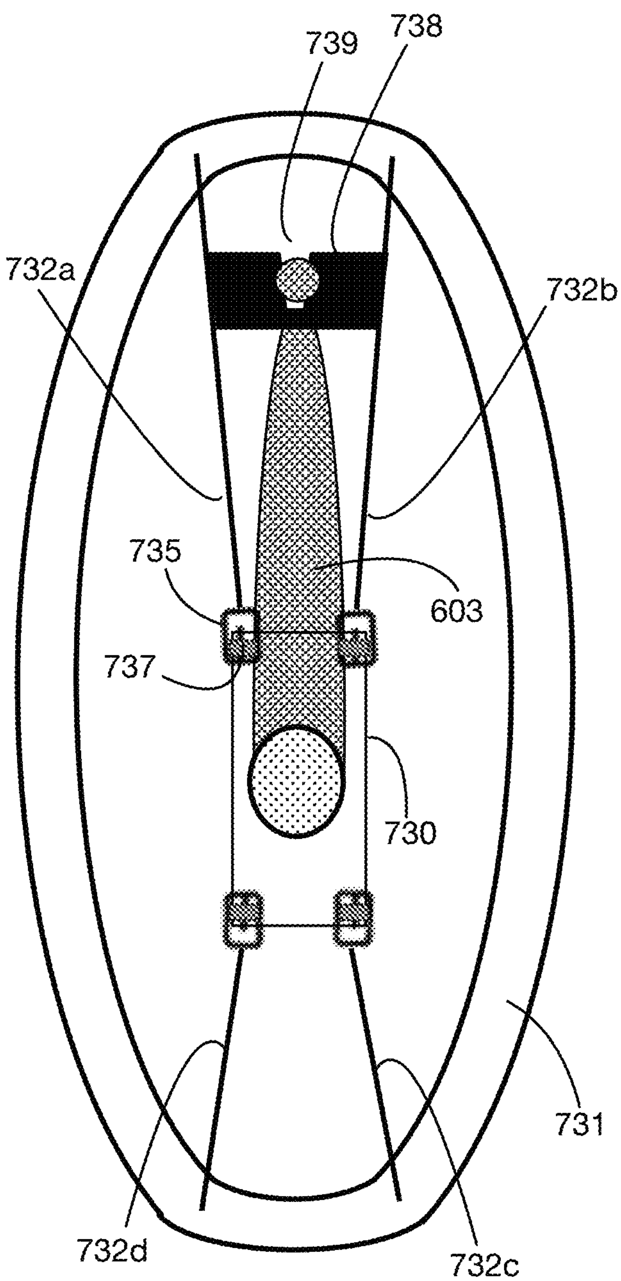
FIG. 7G shows a top view of another illustrative embodiment of a single-use device, multi-use device or garment, or multi-use device or garment with attached single-use sheath that enables "safe sex" with or without penetration, featuring control lines attached to a waistband that temporarily attach to loops on a flange of the open end of the tubular element.
Figure 7H:
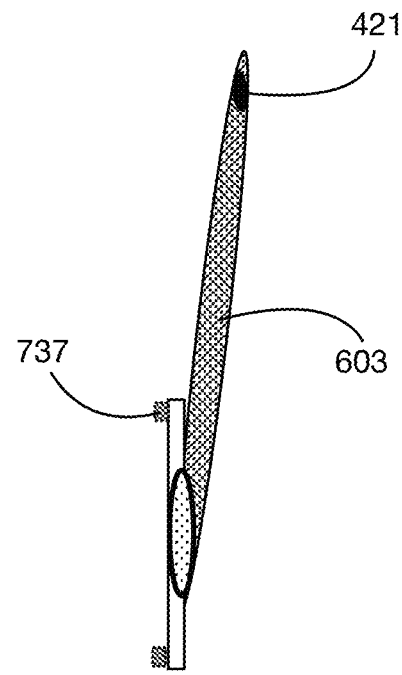
FIG. 7H shows a side view of the embodiment of FIG. 7G with the sheath interior to the device or garment.

FIGS. 7G and 7H illustrate another embodiment with a device 730, which may be for example a small panel of material such as a flange around the opening to tubular element 603, that attaches to a waistband 731 using control lines. FIG. 7G shows a top view, and 7H shows a side view. In this embodiment, four lines 732*a* through 732*d* are attached to the waistband 731 (for example by being sewn into the waistband or otherwise attached permanently or temporarily). Clips or hooks (or other attachment mechanisms) at the free end of the control lines may attach to device 730, for example at the four corners as shown in FIG. 7G. For example, in FIG. 7G control line 732*a* has a hook 735 that attaches through loop 737 at the upper left corner of device 730. Similar attachment may be performed at the other corners. In this embodiment, a button-&-notch-type mechanism 738 (similar to the mechanism illustrated in FIGS. 4L through 4O) may be used to attach the closed end of the tubular element 603. Notch mechanism 738 may for example be attached to one or more control lines, or otherwise attached to waistband 731. A button or similar item 421 may be placed in the closed end of tubular element 603, and placed into the notch 739 to secure the closed end. In this embodiment, the material of device 730 is directly coupled to the open end of tubular element 603; the closed end of tubular element 603 is coupled indirectly to device 730 via coupling of the device 730 to waistband 731 via control lines, and coupling of the closed end of tubular element 603 to notch mechanism 738 that is coupled to the waistband 731. In one or more embodiments the device may include a fully integrated tubular element; in one or more embodiments the device may comprises a base panel with a hole into which a separate tubular element (e.g., condom) may be temporarily attached.

Figure 7I:
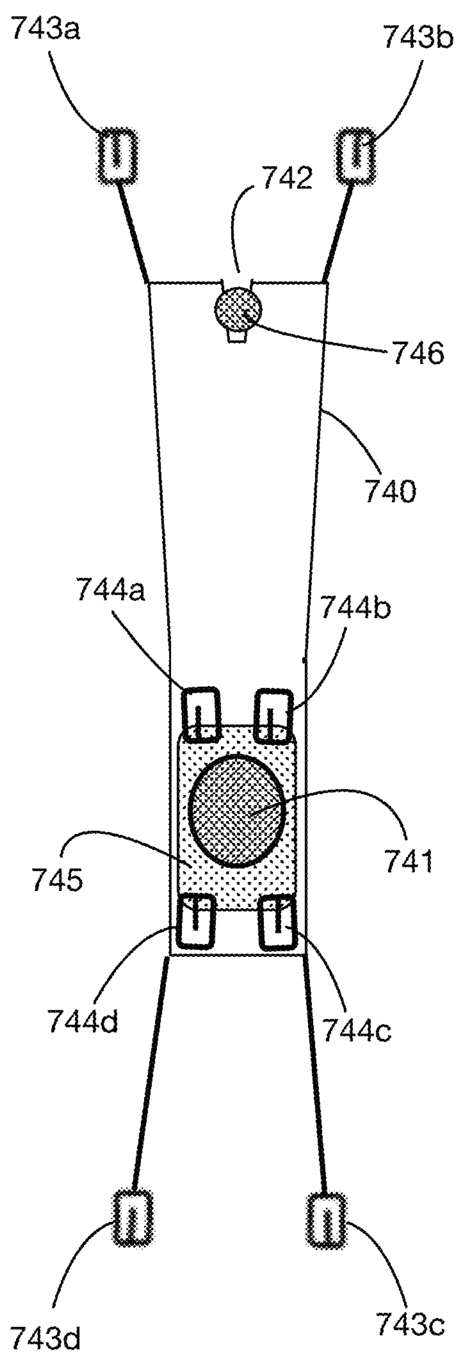
FIGS. 7I and 7J show top views of another illustrative embodiment of a single-use device, multi-use device or garment, or multi-use device or garment with attached single-use sheath that enables "safe sex" with or without penetration, featuring control lines that attach to a waistband and that temporarily attach to loops on a flange of the open end of the tubular element.
Figure 7J:
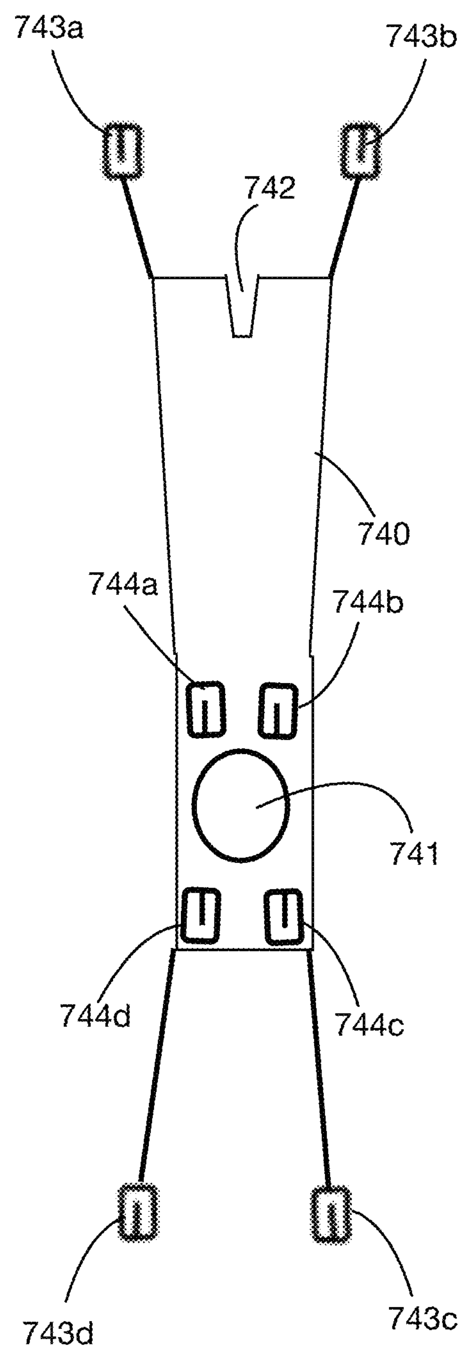

FIGS. 7I and 7J illustrate an embodiment with a panel of material 740 that has an opening 741 at one end, and a notch-type mechanism 742 at the other end. FIG. 7J shows the device without a tubular element, such as a condom, installed; FIG. 7I shows the device with a tubular element installed. Clips or hooks (or another attachment mechanism) 743*a* through 734*d* may for example be used to attach device 740 to a waistband or other garment. A tubular element, such as a condom, may be installed in the device and attached at the open end and at the closed end. In the embodiment of FIGS. 7I and 7J, clips 744*a* through 744*d* on the device may attach for example to a flange 745 on the open end of the tubular element; this is shown in FIG. 7I with the flange 745 attached. To attach the closed end of the tubular element to the device, a button or similar item may be placed in the closed end and secured to the notch 742. FIG. 7I shows closed end 746 with a button installed secured through notch 742. These attachment devices 743*a* through 743*d*, 744*a* through 744*d*, and 742 are illustrative mechanisms; one or more embodiments may substitute or add other types of attachment mechanisms for any or all of attachment to a waistband or garment, attachment to the open end of the tubular element, or attachment to the closed end of the tubular element.

Figure 7K:
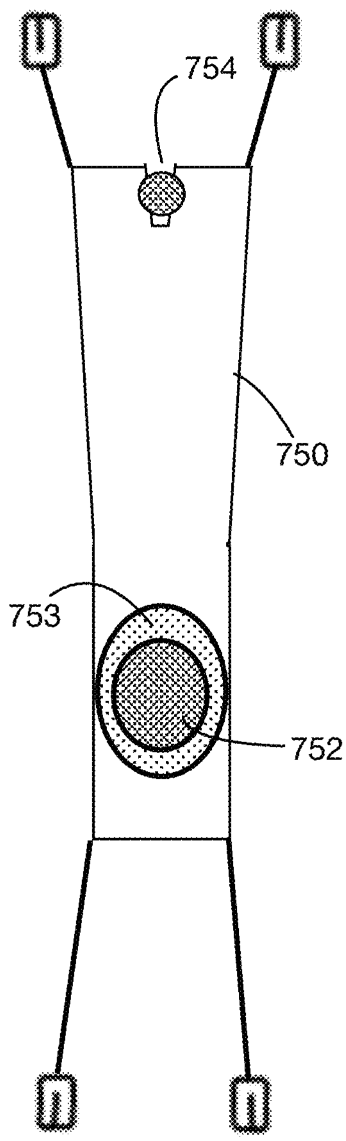
FIG. 7K shows a top view of another illustrative embodiment of a single-use device, multi-use device or garment, or multi-use device or garment with attached single-use sheath that enables "safe sex" with or without penetration, featuring control lines attached to a waistband and an opening that secures the base of a condom because it has a smaller diameter than the base ring of the condom.
Figure 7L:
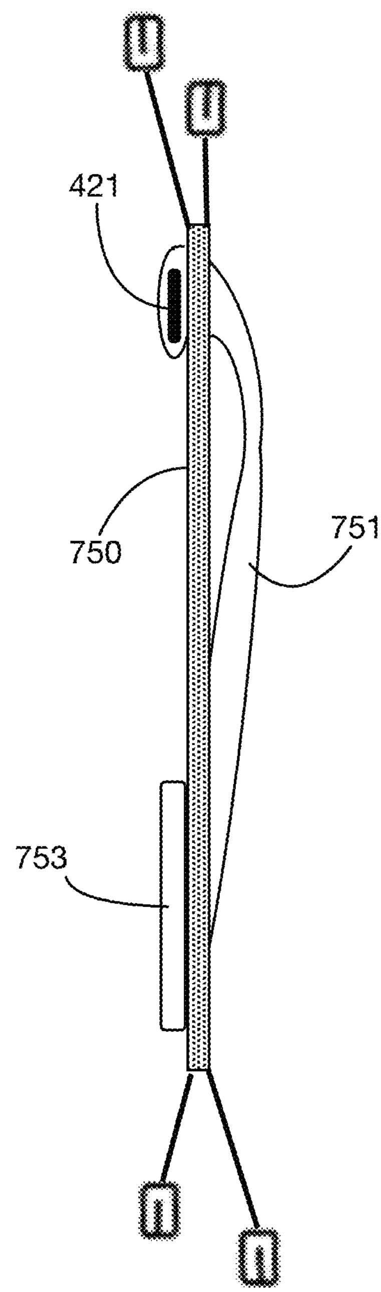
FIG. 7L shows a side view of the embodiment with a tubular element attached.

FIGS. 7K and 7L show a top view and side view, respectively, of a variation on the embodiment of FIGS. 7I and 7J that uses a different attachment mechanism for the open end of a tubular element, such as a condom. FIGS. 7K and 7L both show device 750 with a female condom 751 installed and attached to the device 750. In this embodiment, there are no hooks to secure the open end of the condom. Instead the open end of condom 751 is secured because the opening 752 in the device has a smaller diameter than the diameter of the base ring 753 of the condom. As noted above, the typical base ring diameter on conventional female condoms may be greater than 2.5 inches. As a result, in order to provide secure attachment of the open end of a conventional female condom, the opening 752 may be configured to be less than 2.5 inches in at least one direction. The size and shape of the opening 752 may be impacted by other factors, as well, including the elasticity of the material, for example. In one or more embodiments with a relatively elastic material around the opening, for example, a round opening 752 may have a diameter of less than one inch, leaving plenty of space between the edge of the opening and the base ring on the female condom and relying on the material elasticity to enable the opening to stretch around the girth of a male member inserted into the female condom and through the opening. In one or more embodiments using a somewhat less elastic material around the opening 752, for example, the opening may have the shape of a circle with a diameter between one and two inches, leaving at least a quarter inch around the full circumference of the opening between the opening and the base ring on the female condom. In one or more other embodiments the opening 752 may have the shape of a narrow slit, such that the length of the slit is not substantially limited by the diameter of the base ring because the narrow width of the opening prevents the base ring from being pulled through. Other shapes and sizes for the opening 752 are also conceivable and may be effective, which fall within the scope of the invention. For this type of attachment mechanism for an open end of a female condom, configuring the measurement of the opening 752 in at least one dimension to be less than the width of the base ring on a female condom may ensure that the base ring cannot go through the opening 752.

It is worth noting that this requirement for the dimensions of an opening 752 for attaching an open end of a female condom is within the range of dimensions noted above with regard to ring-type attachment mechanisms that may be used for attaching the open end of male condoms, as described with reference to FIGS. 3A through 3K. As a result, ring-type attachment mechanisms configured to attach the open end of with male-type condoms may also be effective for attaching the open end of female-type condoms. For example, a ring-type attachment mechanism with a diameter of between 1 and 2.25 inches, or that is positioned around an opening with a diameter between 1 and 2.25 inches, could be used to temporarily attach either male-type or female-type condoms or both. In one or more embodiments a ring-type attachment mechanism may be provided for example for temporarily attaching a male condom. Attachment of the closed end of condom 751 may use for example a button-type mechanism 421 placed through notch 754, as described above with respect to FIGS. 7I and 7J.

As noted in various sections above, the features of conventional male and female condoms offer various tradeoffs with respect to their use and performance in non-penetrating sexual applications. As a result, a novel tubular element that integrates key features of conventional male and female condoms may provide key advantages and optimize the performance of a condom-like tubular element for the purposes of non-penetrating sex. For example, such an optimized condom configuration may integrate the functional length more typical of a male condom with the material thickness of a female condom to overcome the relatively fragility of typical male condoms. For example, the optimized condom may have a length from the open end to the closed end that is greater than eight (8) inches. Such an optimized condom configuration may further integrate a tubular diameter and base ring diameter similar to a conventional female condom, thereby enabling simplified attachment of the open end of the condom using mechanisms similar to those described in reference to FIGS. 7K through 7L above. Alternatively, such an optimized condom configuration may integrate a tubular diameter and base ring diameter similar to a conventional male condom, thereby enabling simplified attachment of the open end of the condom using mechanisms similar to those described in reference to FIGS. 3A through 3K above. The optimized condom may further be configured with one or more elements to enable simplified attachment of the closed end using any of the attachment mechanisms discussed herein. For example, the optimized condom may be configured and supplied with a relatively small insert-type element already inserted into the closed end, similar to the way a conventional female condom is supplied with a ring insert already inserted into the closed end. Alternatively, it may be configured with a loop or other mechanism attached to the outside surface of the closed end of the condom. Alternatively, it may not include any specialized element to specifically enable attachment of the closed end of the condom, relying instead on one or more of the many other attachment mechanisms described herein. As such, one or more embodiments may comprise a novel tubular element similar in certain respects to conventional male or female type condoms and configured to enable releasable attachment or coupling of the open and closed ends to a device worn by a first user to enable non-penetrating sex; the tubular element comprising a functional length of eight (8) inches or more, similar to a conventional male condom; a material thickness and material strength similar to that of a conventional female condom; an open end with a relatively wide base ring of a rigidity and diameter similar to a conventional female condom, enabling simplified coupling of the open end to a device or garment through the use of an opening in a surface of the device or garment that is relatively narrow in at least one direction; the closed end of the tubular element being releasably coupled to the garment or device using one or more attachment mechanisms, including but not limited to one or more mechanisms utilizing a relatively small size insert element.

Figure 7M:
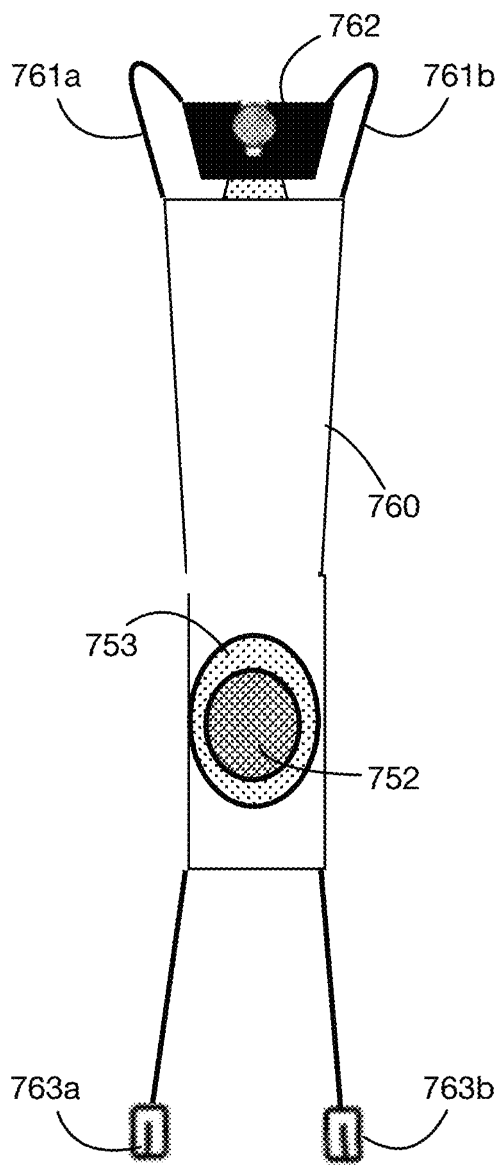
FIG. 7M shows a top view of another illustrative embodiment of a single-use device, multi-use device or garment, or multi-use device or garment with attached single-use sheath that enables "safe sex" with or without penetration, featuring top control lines that wrap around a belt or waistband, and a notch-type mechanism to secure the closed end of the sheath.
Figure 7N:
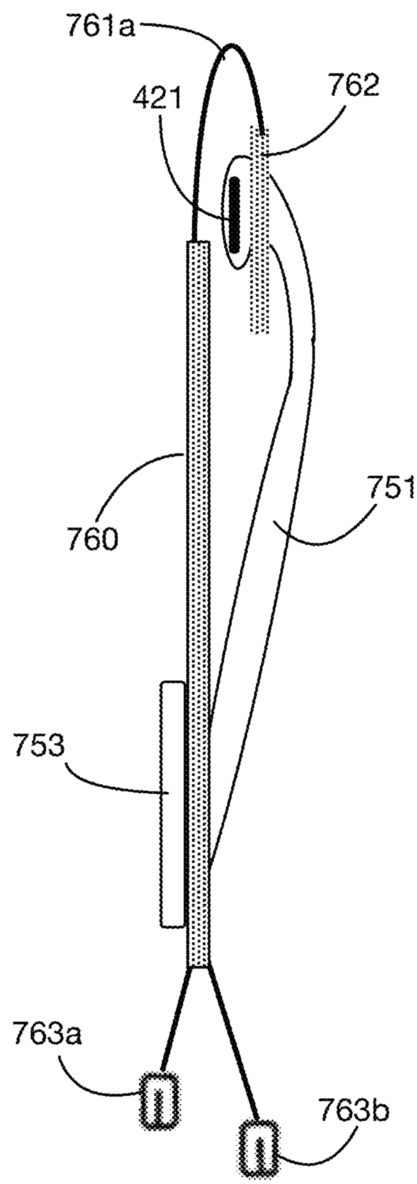
FIG. 7N shows a side view of the embodiment with a tubular element attached.

FIGS. 7M and 7N show a variation of the embodiment of FIGS. 7K and 7L with a different attachment mechanism between the top of the device and the waistband or belt. In this embodiment, the top of the device 760 is not secured to a waistband or belt using clips or hooks, but by wrapping the end of the device over a waistband or belt. For example, the device may have lines 761*a* and 761*b* connecting a lower panel to an upper notch panel 762, and these lines may be wrapped over a waistband or belt. The notch panel 762 (or a similar mechanism for attaching the closed end of condom 751) may for example hang down from the inside of the waistband or belt while the rest of the device hangs down from the outside of the belt (or vice versa). The bottom end of the device 760 may be secured (e.g., to the back of the waistband) using for example clips 763*a* and 763*b*.

Figure 7O:
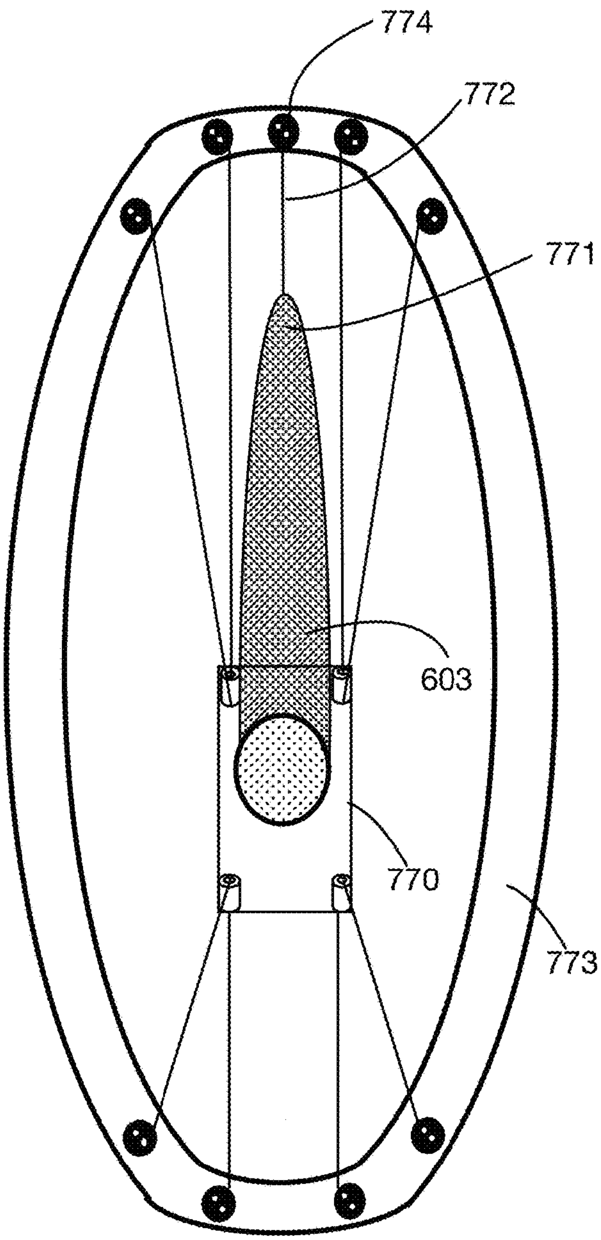
FIG. 7O shows a top view of another illustrative embodiment of a single-use device, multi-use device or garment, or multi-use device or garment with attached single-use sheath that enables "safe sex" with or without penetration, featuring a flange-type element at the opening of the tubular element with attachment points for control lines and a separate control line that extends from the other end of the tubular element.
Figure 7P:
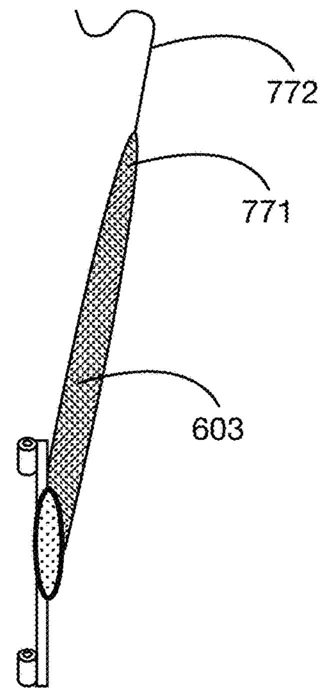
FIG. 7P shows a side view of the embodiment with a tubular element attached.

FIGS. 7O and 7P show an embodiment that is a variation of the embodiment illustrated in FIGS. 7C and 7D. FIG. 7O shows a top view and FIG. 7P shows a side view. Major differences between the embodiment of FIGS. 7O/7P and the embodiment of FIGS. 7C/7D are (i) the base panel 770 of the device does not extend along the full length of the tubular element 603 and (ii) the closed end 771 of the tubular element 603 is attached using a string/cord or similar element 772 that is permanently affixed to the tubular element 603 and is temporarily attached to the waistband 773 by wrapping the string around a button 774, or by any other attachment mechanism.

Figure 7Q:
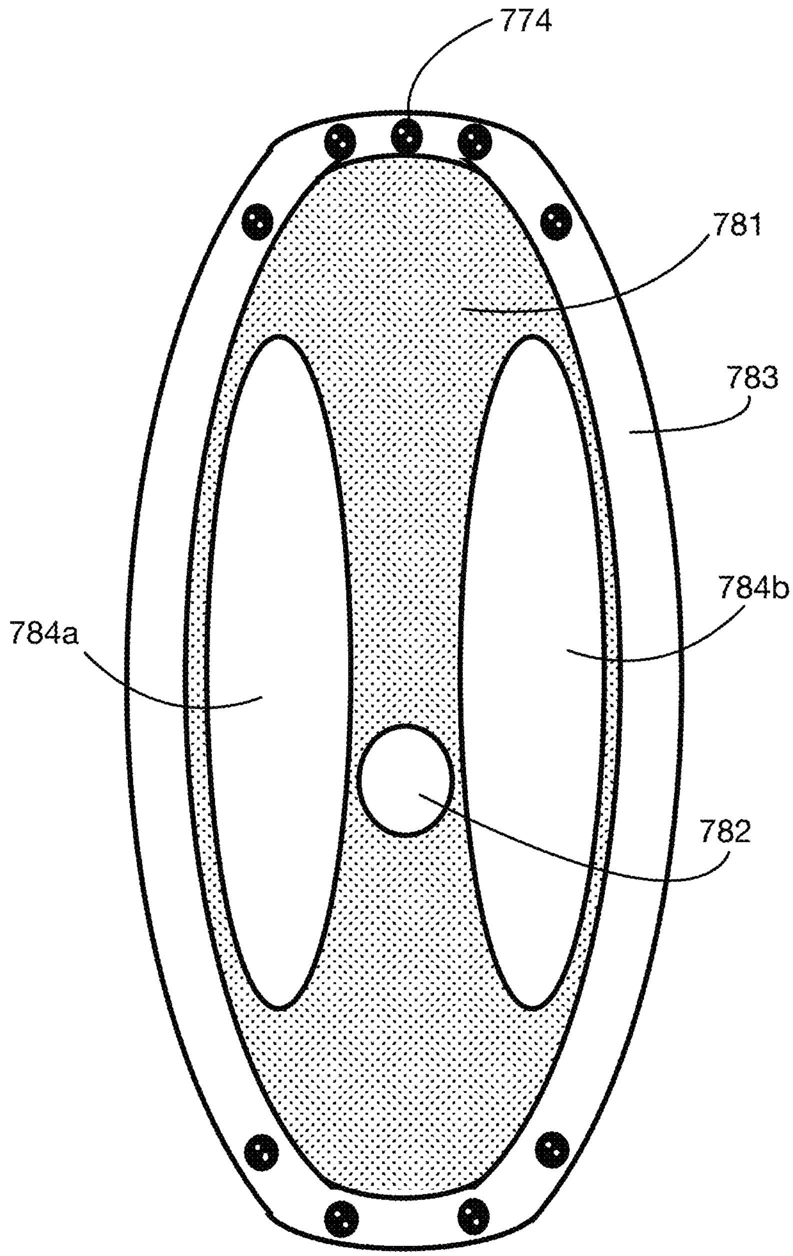
FIG. 7Q shows an illustrative embodiment of a multi-use garment with integrated control line attachment mechanisms (illustrated as buttons) and an opening to allow the tubular portion of a single or multi use sheath element to pass into the interior of the garment while the base portion of the sheath element remains on the exterior of the garment.

FIG. 7Q shows a top view of an embodiment that is a variation of the embodiment illustrated in FIGS. 7O and 7P. In this embodiment the material 781 in which opening 782 for a condom is configured is part of an integrated garment and is attached to waistband 783. Opening 782 may for example allow the tubular portion of a condom (or similar tube) to pass into the inside of the garment while the base remains on the exterior of the garment. Material 781 includes leg holes 784*a* and 784*b*. The top end of a condom or similar tube may for example be attached to a button or other mechanism 774 on the waistband via a string or cord, as in FIGS. 7O/7P.

Figure 7R:
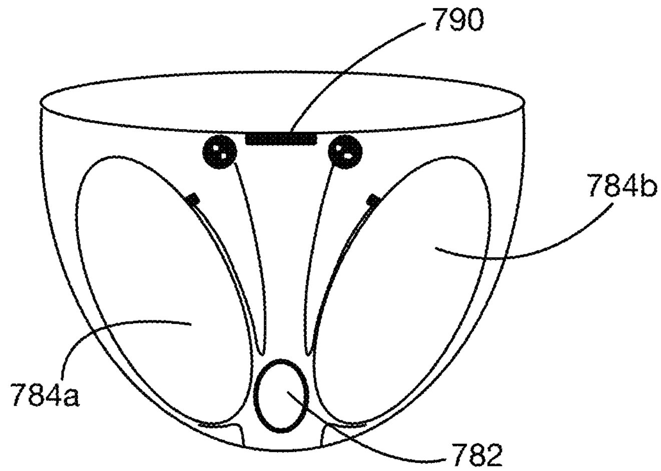
FIG. 7R shows a front view of an illustrative embodiment of a multi-use garment configured to accept a single-use sheath that can be temporarily affixed onto or installed into the garment.
Figure 7S:
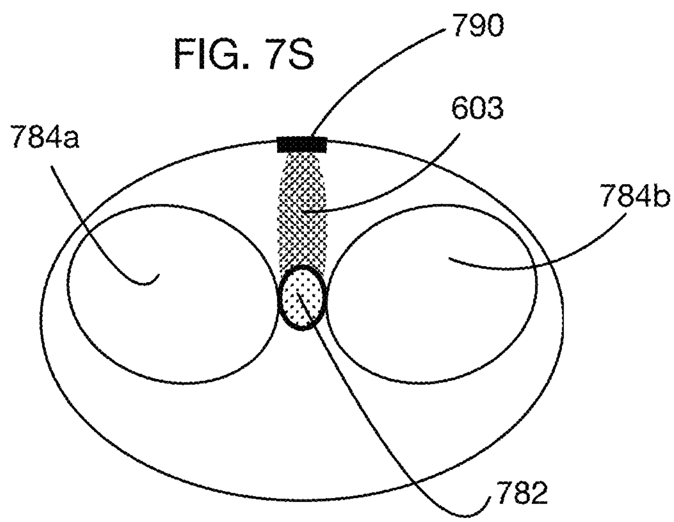
FIG. 7S shows a top view of the embodiment of FIG. 7R.
Figure 7T:
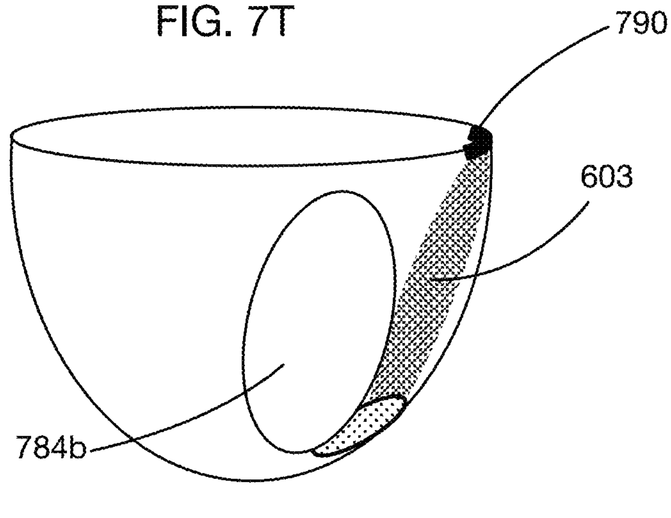
FIG. 7T shows a side view of the embodiment of FIG. 7R.

FIGS. 7R, 7S, and 7T show front, top, and side views, respectively, of a similar embodiment to that of FIG. 7Q, where the attachment mechanism 790 for the closed end of a condom may not necessarily require a string or cord on the closed end. (Attachment mechanism 790 may for example be a loop-and-fold type mechanism, a button or other insert type mechanism with a notch or button hole, or any other attachment mechanism such as those described above.) FIGS. 7S and 7T show the device with a condom 603 inserted and attached. The closed end of condom 603 is attached to mechanism 790, and the open end is attached to or secured against opening 782.

In each of the example embodiments 6A through 7T the device may benefit from positioning the length and closed end (as illustrated) of the tubular element between the first user's body and an outside layer of the device or an outside layer of a garment, though which the tubular element passes. As a result, each of these example embodiments may benefit from a compressive force applied by the outside layer of material—material of the device or material of the garment—against the tubular element and against the first user's body. As a further result, the tubular element may be manufactured from a relatively thin material or comprise a conventional condom without compromising compressive stimulation of the second user's member and with the added benefit of enhancing the stimulation and transmission of sensations between the users.

Figure 8A:
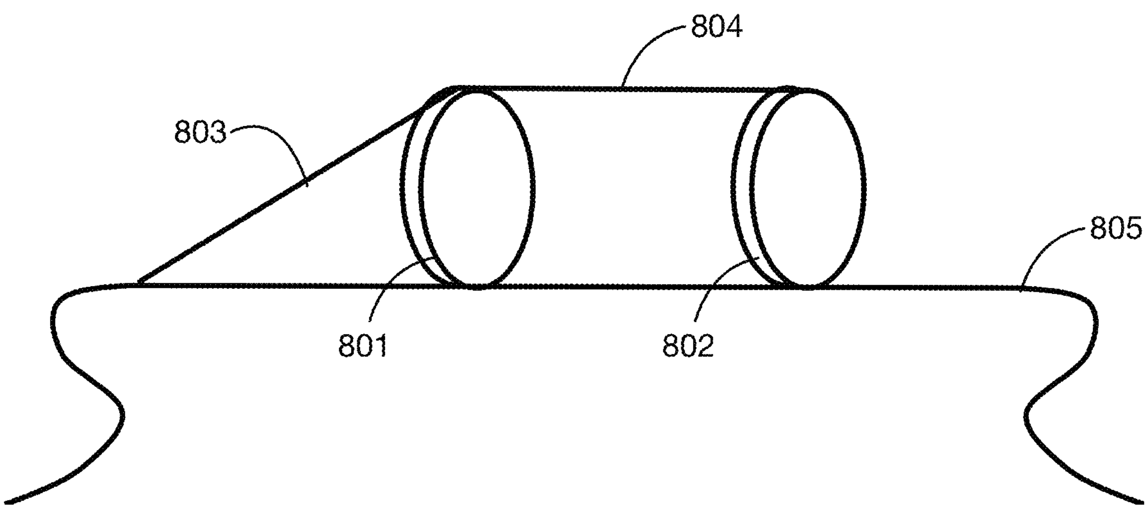
FIG. 8A shows an illustrative embodiment of a device enabling a sheath to be attached to or otherwise partially controlled by a first user.
Figure 8B:
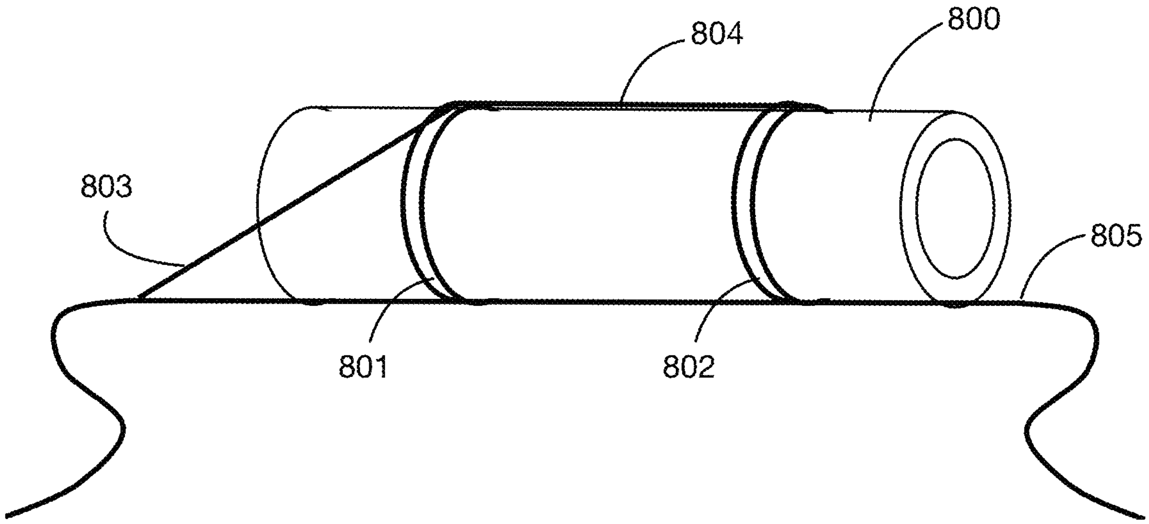
FIG. 8B shows the device of FIG. 8A temporarily attached to a tubular element or device.

FIGS. 8A and 8B illustrate an embodiment enabling a first user to be connected to or otherwise at least partially control the position and/or movement of a detachable element or device that is tubular, sheath-like, or sleeve-like in form and that is configured to enable insertion of a second user's penis. FIG. 8A illustrates an embodiment capable of functioning with a detachable tubular element 800. FIG. 8B illustrates the embodiment with the detachable tubular element 800 installed.

The embodiment illustrated in FIG. 8A may include one or more elements representing a strap, a ribbon of material, or a surface of a mechanism that otherwise enables the device to be worn by a first user, to be connected to a first user, or to otherwise enable a first user to at least partially control the position and/or movement of the device. The control element(s) may be constructed from various types of materials and may be connected to various types of additional elements (e.g., elements enabling a first user to wear or otherwise provide greater control of the device) within the scope of the invention. For example, the control elements may comprise ribbons of fabric, or alternately a rigid or semi-rigid material, that may be held in a first user's hands to provide at least partial control of the position and/or movement of the attached tubular element. Alternately, the control elements may comprise ribbons of fabric, or alternatively rigid or semi-rigid materials, capable of being temporarily fastened or releasably coupled to a garment resembling underwear or other device that is worn by a first user such that the position and/or movement of the first user's body affects or provides at least partial control of the position and/or movement of the attached tubular element. In various embodiments, the control elements may be configured to extend out from between openings in a second user's clothing while the second user's male member is inserted into the tubular element. In this way, the control elements may be configured to be accessible to a first user from outside the second user's clothing and may enable the first user to exert at least partial control over the movement and/or position of the tubular element exclusively from outside of the second user's clothing while the tubular element is positioned under the second user's clothing on the male member of the second user. As a result, various embodiments may enable a first user to control the stimulation provided to the second user by the tubular element without being exposed to any portion of the second user's body or male member and without being in direct contact with any portion of the second user's body or male member.

In the illustrative embodiment shown in FIGS. 8A and 8B, element or elements 805 may for example be a strap or ribbon enabling temporary attachment to a garment worn by a first user. The strap or ribbon may also or alternatively be controlled by the first user in order to control the position of movement of the tubular element 800. The embodiment may also include one or more mechanisms enabling temporary attachment of a tubular element or device 800. The attachment mechanisms are illustrated as two circular bands 801 and 802 affixed to the control element 805 and configured to fit securely around the tubular element or device 800 at two different points along the length of the tubular element. Guide straps or ribbons 803 and 804 may attach to the bands 801 and 802 to provide additional control. The bands 801 and 802 may be constructed from various types of materials. In one or more embodiments, at least a portion of the attachment bands 801 and 802 may be constructed from an elastic material to provide compressive force against the tubular element 800, to increase friction with the tubular element to enhance the security of the attachment, and/or to accommodate variability in the diameter of the tubular element. The ability to accommodate variability in the diameter of the tubular element or device may be useful for example because alternate tubular elements may have different diameters, because a single tubular element may have variable diameters along the length of the element, or because a single tubular element may have variable width depending on the insertion of a penis, for example. The bands 801 and 802 may include various types of features that further enhance the security of attachment to the tubular element. For example, the bands may have features that fit into grooves molded into the tubular element 800 to further limit slippage between the bands and the tubular element. Alternate configurations, for example with greater or fewer number of bands may be distributed in various ways along the length of the tubular element or at the ends of the tubular element. Alternatively, the attachment mechanism may comprise cylindrical piece of material designed to envelop or extend along the entire length of the tubular element. Alternate types of attachment mechanisms are also conceivable within the scope of the invention. Such alternatives include, but are not limited to, various types of straps, clips, buttons, hook-and-loop type fasting systems, grooves or slots into which elements integrated with the tubular element may be fitted, elements configured to fit into various types of grooves or slots that are integrated with the tubular element, or other types of mechanisms enabling temporary attachment or fastening of a tubular element to one or more control elements.

Figure 9A:
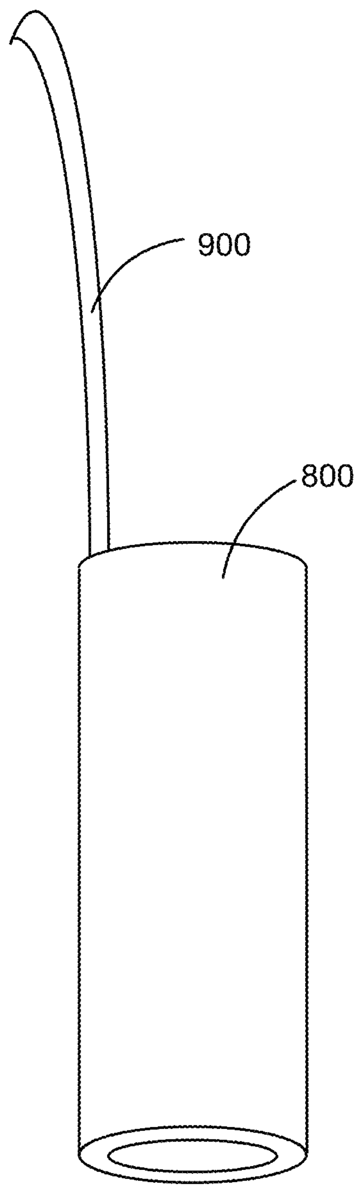
FIG. 9A shows an illustrative embodiment of a device enabling a sheath to be attached to or otherwise partially controlled by a first user while the penis of a second user is inserted into the sheath. In the embodiment shown in FIG. 9A, the control element is permanently affixed to the tubular element.
Figure 9B:
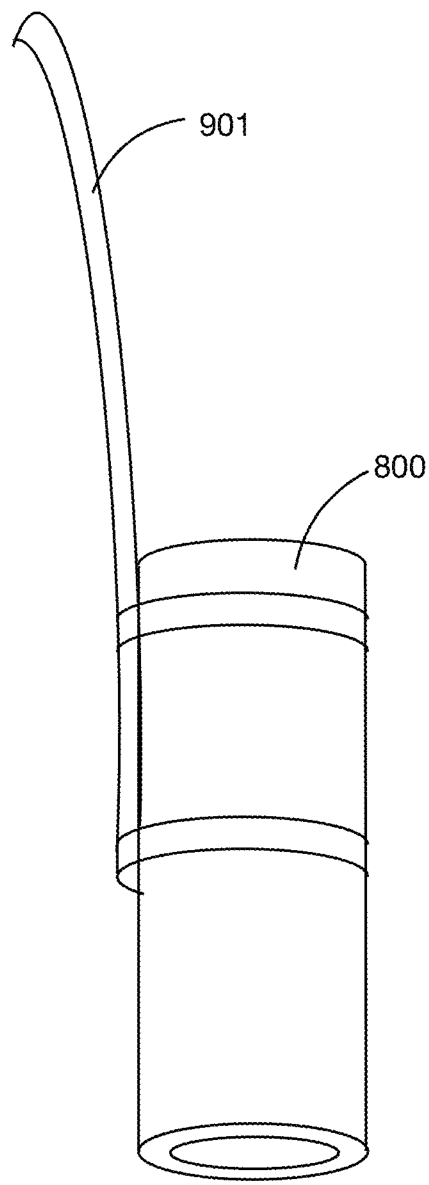
FIG. 9B shows a variation of FIG. 9A with the control element temporarily affixed to the tubular element using elastic straps.

FIGS. 9A and 9B illustrate additional embodiments enabling attachment to or partial control by a first user of a tubular element 800 into which the penis of a second user may be inserted. FIG. 9A illustrates an embodiment in which the tubular element 800 is permanently affixed to the control element, while FIG. 9B illustrates an embodiment in which the tubular element 800 may be temporarily attached to the control mechanism.

In the embodiments illustrated in FIGS. 9A and 9B, the control element, which enables at least partial control of position and/or movement of the tubular element, may comprise a rigid or semi-rigid shaft, handle, or flattened stick that extends outward from one end of the tubular element. A potential benefit of configuring the device with a rigid or semi-rigid control device at one end of the tubular element 800 is that the control element may in some situations provide more precise control of the position and/or movement of a tubular element 800 when the tubular element is constructed from a flexible material. A further potential benefit is to enhance the ability for the control element to be made accessible from outside the clothing of the second user and enable effective control of the movement and/or position of the tubular element while the penis of the second user is inserted into the tubular element under the clothing of the second user. In this way, the embodiments illustrated in FIGS. 9A and 9B can be used while the second user is fully clothed, without exposing the second user's body and without direct bodily contact between the second user and the controlling user, who may be the first user described above.

The semi-rigid control element may extend part way or all the way down the length of the tubular element. As illustrated in FIG. 9A, the control element 900 may extend part way down the length of the tubular element 800 within the sidewall of the tubular element. As illustrated in FIG. 9B, the control element 901 may extend part way down the length of the tubular element 800 along the outside surface of the tubular element. The control elements illustrated in both FIGS. 9A and 9B may configured to be permanently affixed to the tubular element 800 or detachable/temporarily attachable to the tubular element using various types of attachment elements and mechanisms, as noted above.

As noted above, a potential benefit of configuring the control element as a semi-rigid shaft extending from the end of the tubular element is to enhance the ability for the control element(s) to be positioned to protrude out from between the clothes of a second user and/or be accessible from outside the second user's clothes while the second user's penis is inserted into the tubular element. For example, a second user may position the tubular element 800 under their pants, insert their penis into the tubular element and position the control element 900 or 901 to protrude out of their clothes at their waist, between their pants and shirt. This may enable attachment of the control element(s) of the tubular element to a first user and/or enable at least partial control of the tubular element by a first user while a second user's penis is inserted into the tubular element under their clothes. As such, the device may be controlled by a first user, for example a first user that is an adult entertainer (e.g., to enhance the performance of a "lap dancer"), while both the second user and the first user are fully clothed and without requiring the first user to either touch or be exposed to the genitals or any portion of the second user's body.

Figure 9C:
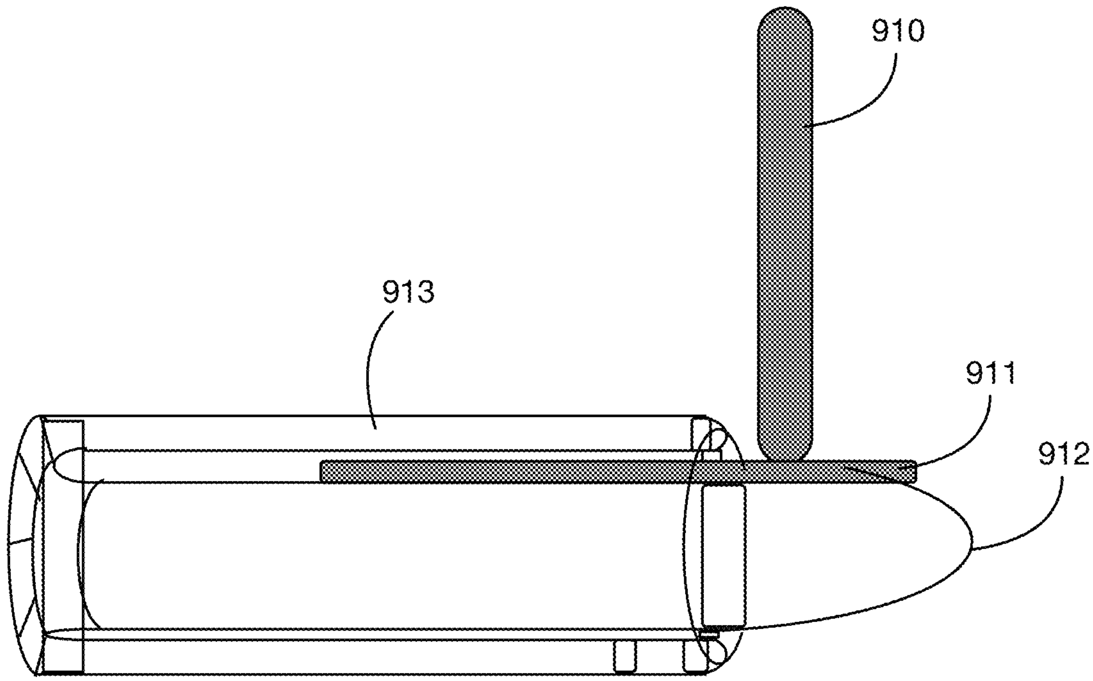
FIG. 9C shows an illustrative embodiment of a two-layer sheath with a partial sheath stiffener and a control rod or control straps, where the external layer may completely or only partially surround the internal tubular element.

FIG. 9C shows an example of a multi-layer version of the embodiments illustrated in FIGS. 9A and 9B. In this embodiment, the device has two concentric tubular elements 912 and 913 that are connected to each other at the base. The connection at the base is one of multiple locations where the concentric tubular elements may be connected. Alternatively, for example, the tubular elements may be connected at the top, at various points along their length, at the base, as illustrated, or at multiple locations. The one or more connections between the concentric tubular elements may connect the tubular elements around their full circumference or only at certain locations around the circumference of the concentric tubular elements. The one or more connections between the tubular elements at the base and/or at other locations may be flexible/elastic so that the inner tubular element 912 may slide relatively freely for some distance along the inside of the outer tubular element 913. Alternatively, the connections may comprise elements enabling elements of the connections between the concentric tubular elements to slide along each other. For example, the connection may comprise an element attached to or embedded in the surface of one of the tubular elements that fits into a groove-type element attached to or embedded within the surface of the other tubular element, such that the element attached to one tubular element can slide along the groove-type element. In this and other related ways, the points of connection between the concentric tubular elements may comprise mechanisms that slide longitudinally, thereby enabling the inner tubular element 912 to slide relatively freely for some distance along the inside of the outer tubular element 913. The inner surface of outer tubular element 913 and the outer surface of inner tubular element 912 may be configured to permit sliding of these surfaces against each other. A control shaft 911 may be attached to the inner tubular element 912, and coupled to control element 910, which may for example be a rod or any other mechanism that can be controlled or can transmit control inputs and control forces from a first user or controlling user to the inner tubular element. In the example illustrated, movement of the control element 910 results in movement of the control shaft 911, which moves the inner tubular element 912 relative to the outer tubular element 913 and relative to a second user's member that is inserted into the inner tubular element. In one or more use cases, the outer tubular element 913 may be in a relatively fixed position with respect to the second user's body and clothing, while the inner tubular element 912 may move along the second user's member in response to control forces applied to the control shaft 911 via the control element 910. The external surface of outer tubular element 913 may be in contact with the second user's body or clothes. In one or more embodiments this outer surface or a portion of the outer tubular element 913 may be made of a material that protects the second user from discomfort caused by the control shaft 911. In one or more embodiments a portion of the inside tube 912 may be manufactured from a material that is sufficiently stiff that a separate "shaft" 911 is not required. The goal of either the partial or complete stiffening of the inner tubular element or a shaft is to ensure that the inner tube 912 actually slides (instead of stretching) when force is applied to the control element 910.

Figure 9D:
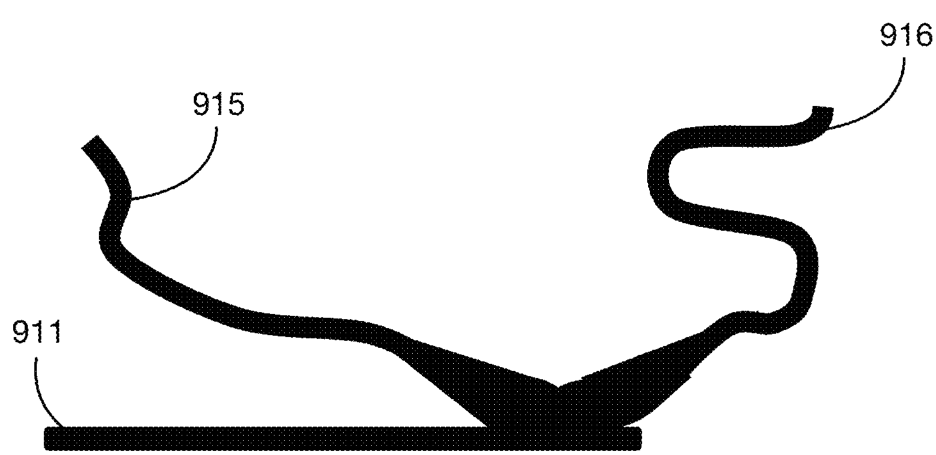
FIG. 9D shows a different embodiment of a control element that may be used with the embodiment of FIG. 9C.

FIG. 9D shows an alternative embodiment of a control element. In this embodiment the control element may for example comprise flexible fabric strips or straps 915 and 916 coupled to the control shaft 911, as compared to the rigid control rod 910 of FIG. 9C. One or more embodiments may include elements or mechanisms integrated into or attached to a first or controlling user's clothing or body that may enable a first user to apply force to the control element with their body movements, rather than exclusively with their hands. Such mechanism may include, but are not limited to hooks, clips, sleeves, loops, straps, or any similar mechanism to temporarily attach the control elements on the device to the controlling user/first user, their clothing, or any other similar garment. As noted above, configurations that enable the control elements to be accessible to a first or controlling user from outside the clothing of a second user while a member of the second user is inserted into the tubular element enables the first or controlling user to at least partially control the movement of the tubular element and the stimulation of the second user's member without being directly exposed to and without coming in direct physical contact with the second user's member or any other part of the second user's body.

Figure 9E:
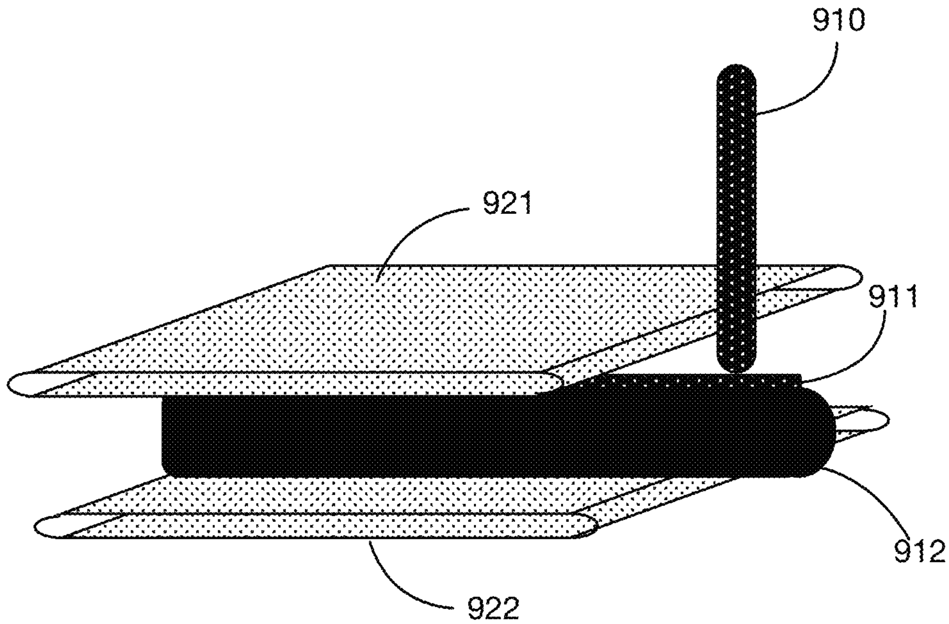
FIG. 9E shows another illustrative embodiment of a two-layer sheath with a partial sheath stiffener and a control rod or control straps, where the external layer does not surround the internal tubular element.

FIG. 9E shows a variation of the embodiment of FIG. 9C. In this embodiment, inner tubular element 912 is controlled by a control element 910 coupled to a control shaft 911, as in FIG. 9C. However, unlike FIG. 9C, in this case the inner tubular element 912 does not slide against an outer tubular element; instead it slides between two outside layers of material 921 and 922. The inner surface of these layers may be configured to slide against the outer surface of inner tubular element 912. As illustrated in FIG. 9E, these layers may be configured to comprise relatively flat surfaces; however, they may also be configured to represent curved surfaces, partial cylinders, or any other convenient shape that enables the inner tubular element 912 to slide along the inside surfaces of the outside layers of material 921 and 922. In some configurations the layers 921 and 922 may remain fixed against the body/clothing of the second user, within which the inner tubular element 912 may slide. In one or more embodiments the layers 921 and 922 may have grooves or channels, for example, or other mechanisms to enable movement of inner tubular element 912 in a longitudinal direction.

Figure 10A:
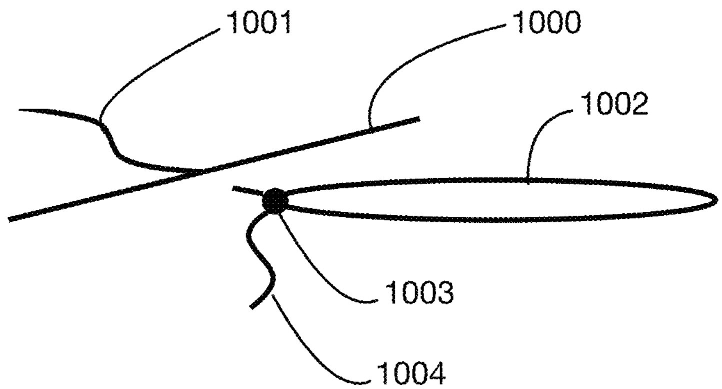
FIG. 10A shows an illustrative embodiment of a ribbon or string-based attachment mechanism for the closed end of a condom.
Figure 10B:
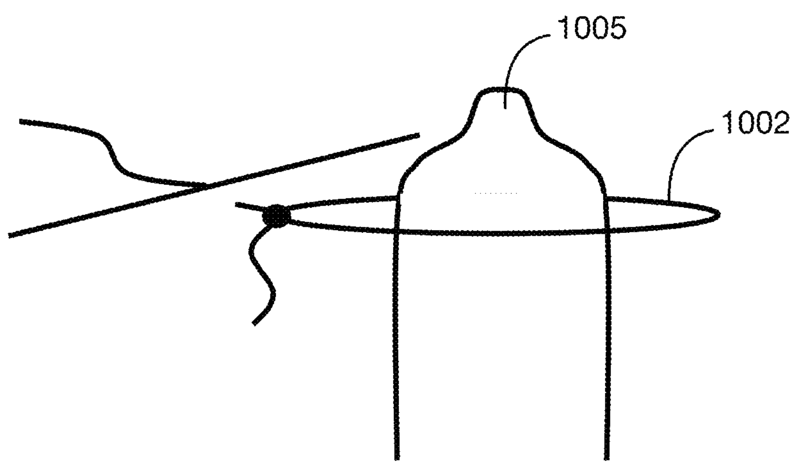
FIGS. 10B, 10C, 10D, 10E, and 10F show illustrative steps in inserting and attaching a condom to the device of FIG. 10A.
Figure 10C:
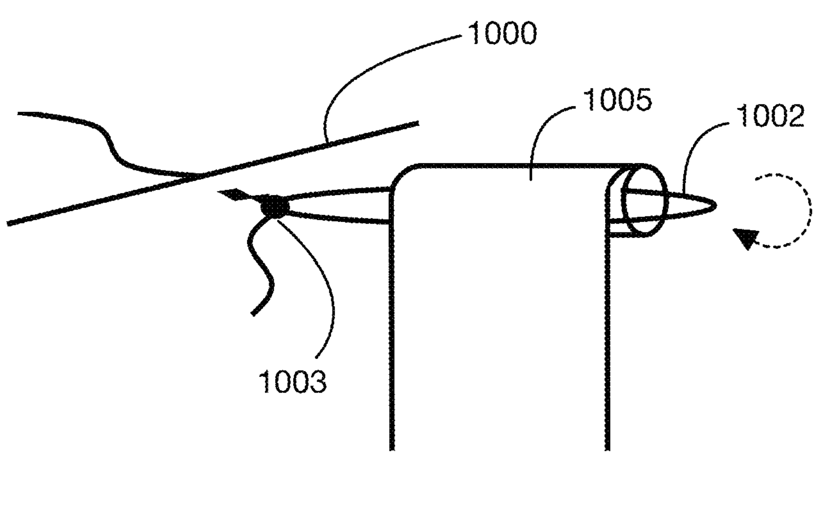
Figure 10D:
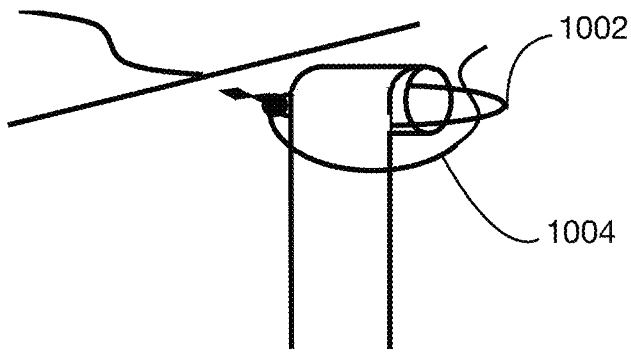
Figure 10E:
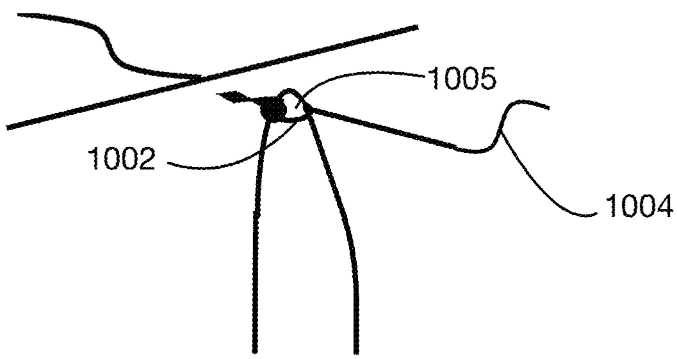
Figure 10F:
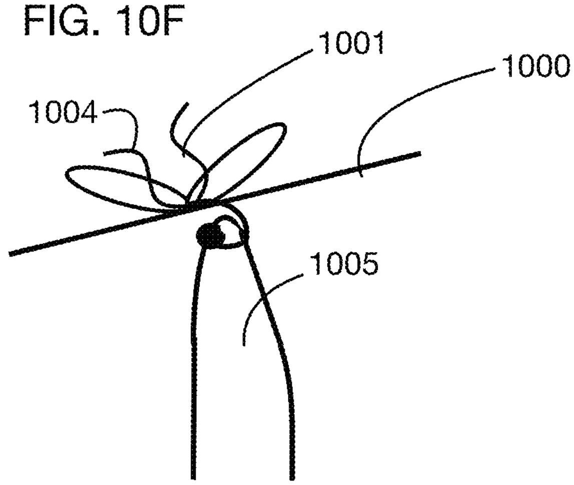

FIG. 10A illustrates an embodiment of a ribbon or string-based attachment mechanism to attach the closed end of a condom to a waistband or similar garment or device. A ribbon 1001 passes through waistband 1000, and a loop 1002 is formed by passing the ribbon through a knot 1003, such as a slip knot for example, leaving a loose end 1004. FIGS. 10B through 10F show illustrative steps to attach a condom to this embodiment. In step 1, shown in FIG. 10B, the closed end of condom 1005 is inserted through loop 1002. In step 2, shown in FIG. 10C, loop 1002 is rotated, for example 2 to 3 times, twisting the ribbon between the knot 1003 and the waistband 1000. In step 3, shown in FIG. 10D, the loose end 1004 of the ribbon is threaded through the end of loop 1002. In step 4, shown in FIG. 10E, the loop 1002 is tightened, cinching the condom 1005 into the loop. In step 5, shown in FIG. 10F, the loose ends 1001 and 1004 of the ribbon are tied together to securely attach the condom 1005 to the waistband 1000.

While the invention herein disclosed has been described by means of specific embodiments and applications thereof, numerous modifications and variations could be made thereto by those skilled in the art without departing from the scope of the invention set forth in the claims.

What is claimed is:

1. An apparatus comprising:

a tubular element adapted to allow non-penetrating sex between a first user and a second user wherein said tubular element comprises an open end and a closed end;

a garment configured to be worn by said first user wherein said garment comprises an interior surface facing said first user and an exterior surface facing away from said first user and wherein said garment comprises a hole therethrough;

a first element configured to fixedly or releasably couple with said open end of said tubular element at a first location on said garment;

a second element configured to fixedly or releasably couple on said closed end of said tubular element at a second location on said garment that differs from said first location; wherein said tubular element is external to all natural orifices of said first user during non-penetrating sex.

2. The apparatus of claim 1 wherein said first element and said second element are both fixedly attached to said garment.

3. The apparatus of claim 1 wherein said first element and said second element are both portions of a single physical structure.

4. The apparatus of claim 1 wherein said first element and said second element are integrated into a single device.

5. The apparatus of claim 1 wherein said first element and said second element use a same attachment type.

6. An apparatus comprising:

a tubular element adapted to allow non-penetrating sex between a first user and a second user wherein said tubular element comprises a condom having an open end and a closed end;

a garment configured to be worn by said first user wherein said garment comprises an interior surface facing said first user and an exterior surface facing away from said first user and wherein said garment comprises a hole therethrough;

a first element configured to fixedly or releasably couple with said open end of said tubular element at a first location on said garment;

a second element configured to fixedly or releasably couple on said closed end of said condom at a second location on said garment that differs from said first location; wherein said condom is external to all natural orifices of said first user during non-penetrating sex.

7. The apparatus of claim 6 wherein said condom is a male condom.

8. The apparatus of claim 7 wherein said male condom comprises lubrication wherein said male condom is coupled to said first element and said second element inside-out to enable a member of said second user to readily move in and out of said condom while said first element and said second element immobilize said condom relative to said first user.

9. The apparatus of claim 6 wherein said condom is a female condom.

10. The apparatus of claim 6 wherein said first element further comprises:

an annular ramp of comprising an elastomeric material, or a flange configured to couple to said open end of said condom, or a segmented flange configured to couple to said open end of said condom or said flange and a ring wherein said ring is configured to elastically provide force to said condom when placed between said ring and said flange wherein said flange and ring are configured to couple to said open end of said condom, or a plurality of hooks, or said ring with a groove;

and wherein said first element couples with said condom on said open end of said condom by placing a base ring of said condom into said groove, or said ring comprising a plurality of beads connected by one or more elastic elements;

wherein said ring is configured to expand to accommodate one or both of said condom or a member, or an opening smaller than said open end of said condom.

11. The apparatus of claim 6 wherein said condom has one or both of a base ring or a flange on said open end of said condom.

12. The apparatus of claim 6 wherein said second element comprises:

a notch and wherein said condom is coupled with said second element via a small object inside said condom that is larger than said notch, or a button hole and wherein said condom is coupled with said second element via said small object inside said condom that fits through said button hole, or a loop and wherein said condom is coupled with said second element by cinching said condom with said loop, or a roller and wherein said condom is coupled with said second element via said roller, or a surface configured to fold in two dimensions, said loop across one side of said surface and configured to receive said closed end of said condom, an attachment mechanism to secure a left portion of said surface against a corresponding right portion of said surface, or an attachment element configured to couple with a line, wherein said condom is configured with said line extending from said closed end of said condom, wherein said attachment element is coupled to an end of said line opposite said closed end of said condom.

13. The apparatus of claim 6 wherein said first element couples to a waistband in a front portion and a rear portion of said first user with connection elements that extend from said first element to said waistband and wherein said second element couples to either said waistband close to said front portion or said rear portion of said first user.

14. The apparatus of claim 6 wherein said first element couples to said garment in a front and rear portion of said first user with material that extends from said first element to at least one leg of said first user and wherein said second element couples to said first user at a location distal to said first element.

15. The apparatus of claim 6 wherein said first element is located on an outer portion of said garment and said second element is located on an inner portion of said garment.

16. The apparatus of claim 6 wherein said first element is located on an outer portion of said garment and said second element is located on said outer portion of said garment.

17. The apparatus of claim 6 wherein said first element and said second element are both portions of a single physical structure.

18. The apparatus of claim 6 wherein said first element and said second element are integrated into a single device.

19. The apparatus of claim 6 wherein said first element and said second element use a same attachment type.

20. An apparatus comprising:

a tubular element adapted to allow non-penetrating sex between a first user and a second user wherein said tubular element comprises a condom having an open end and a closed end;

a garment configured to be worn by said first user wherein said garment comprises an interior surface facing said first user and an exterior surface facing away from said first user and wherein said garment comprises a hole therethrough;

a first element configured to fixedly or releasably couple said open end of said tubular element at a first location on said garment;

a second element configured to fixedly or releasably couple on said closed end of said condom at a second location on said garment that differs from said first location; wherein said condom is external to all natural orifices of said first user during non-penetrating sex;

wherein said first element further comprises an annular ramp of comprising an elastomeric material, or a flange configured to couple to said open end of said condom, or a segmented flange configured to couple to said open end of said condom or said flange and a ring wherein said ring is configured to elastically provide force to said condom when placed between said ring and said flange wherein said flange and ring are configured to couple to said open end of said condom, or a plurality of hooks, or said ring with a groove;

and wherein said first element couples with said condom on said open end of said condom by placing a base ring of said condom into said groove, or said ring comprising a plurality of beads connected by one or more elastic elements;

wherein said ring is configured to expand to accommodate one or both of said condom or a member, or an opening smaller than said open end of said condom;

and, wherein said second element comprises a notch and wherein said condom is coupled with said second element via a small object inside said condom that is larger than said notch, or a button hole and wherein said condom is coupled with said second element via said small object inside said condom that fits through said button hole, or a loop and wherein said condom is coupled with said second element by cinching said condom with said loop, or a roller and wherein said condom is coupled with said second element via said roller, or a surface configured to fold in two dimensions, said loop across one side of said surface and configured to receive said closed end of said condom, an attachment mechanism to secure a left portion of said surface against a corresponding right portion of said surface, or an attachment element configured to couple with a line, wherein said condom is configured with said line extending from said closed end of said condom, wherein said attachment element is coupled to an end of said line opposite said closed end of said condom.

* * * * *